(12) United States Patent
Kurniawan et al.

(10) Patent No.: US 10,979,401 B2
(45) Date of Patent: Apr. 13, 2021

(54) APPARATUS AND METHOD FOR SHARING PERSONAL ELECTRONIC-DATA OF HEALTH

(71) Applicant: Samsung Electronics Co., Ltd., Suwon-si (KR)

(72) Inventors: Agus Kurniawan, Jakarta (ID); Fajri, Jakarta (ID); Omar Abdillah, Jakarta (ID)

(73) Assignee: Samsung Electronics Co., Ltd., Suwon-si (KR)

( * ) Notice: Subject to any disclaimer, the term of this patent is extended or adjusted under 35 U.S.C. 154(b) by 335 days.

(21) Appl. No.: 15/221,140

(22) Filed: Jul. 27, 2016

(65) Prior Publication Data
US 2017/0177797 A1 Jun. 22, 2017

(30) Foreign Application Priority Data

Dec. 18, 2015 (ID) .............................. P00201508592
May 26, 2016 (KR) ........................ 10-2016-0065074

(51) Int. Cl.
*G16H 10/60* (2018.01)
*H04L 29/06* (2006.01)
*H04W 12/06* (2021.01)

(52) U.S. Cl.
CPC ......... *H04L 63/0428* (2013.01); *G16H 10/60* (2018.01); *H04L 63/0861* (2013.01); *H04L 63/0876* (2013.01); *H04L 63/20* (2013.01); *H04W 12/06* (2013.01)

(58) Field of Classification Search
CPC ....... G06F 19/00; G06F 19/322; H04L 29/06; H04L 63/20; H04L 63/0861; H04L 63/0428

USPC .............................................................. 705/2
See application file for complete search history.

(56) References Cited

U.S. PATENT DOCUMENTS

| | | | |
|---|---|---|---|
| 7,971,055 B2 | 6/2011 | Weeks et al. | |
| 7,974,924 B2* | 7/2011 | Holla | G06F 19/322 705/51 |
| 8,355,970 B2 | 1/2013 | Fox et al. | |
| 2002/0133697 A1* | 9/2002 | Royer | G06F 21/41 713/150 |
| 2002/0156650 A1* | 10/2002 | Klein | G06F 19/3418 705/2 |
| 2004/0049355 A1* | 3/2004 | Maus | A61B 5/0002 702/19 |
| 2004/0199765 A1* | 10/2004 | Kohane | H04L 63/102 713/165 |

(Continued)

FOREIGN PATENT DOCUMENTS

WO 2011045723 A1 4/2011

*Primary Examiner* — Reginald R Reyes
(74) *Attorney, Agent, or Firm* — Jefferson IP Law, LLP

(57) ABSTRACT

A trust management system providing secure communication for storing and sharing personal electronic—data of health (e-health data) and a method thereof are provided. The method includes creating a security policy in accordance with at least one input of a user of the electronic device through a security policy design tool, generating a link for gaining access to the data of health based on the security policy, receiving a transmission request for the data of health using the link from a health data request device, and performing authentication on the transmission request based on the security policy.

14 Claims, 18 Drawing Sheets

(56) References Cited

U.S. PATENT DOCUMENTS

| | | | |
|---|---|---|---|
| 2006/0269061 A1* | 11/2006 | Balasubramanian | ................ C07D 209/88 380/247 |
| 2009/0183008 A1* | 7/2009 | Jobmann | ............... H04L 9/0866 713/186 |
| 2009/0249076 A1* | 10/2009 | Reed | ............ G06Q 30/00 713/181 |
| 2009/0322488 A1* | 12/2009 | Kanagala | ......... H04W 52/0229 340/10.3 |
| 2011/0288874 A1* | 11/2011 | Hinkamp | ............ G06F 21/6245 705/1.1 |
| 2012/0179908 A1* | 7/2012 | Duma | ................... G16H 10/65 713/165 |
| 2012/0197740 A1* | 8/2012 | Grigg | .................... G06Q 20/20 705/16 |
| 2012/0260094 A1 | 10/2012 | Asim et al. | |
| 2012/0300932 A1* | 11/2012 | Cambridge | ........... H04L 9/3234 380/270 |
| 2013/0332899 A1* | 12/2013 | Stewart | .............. G06F 9/44505 717/121 |
| 2014/0075184 A1 | 3/2014 | Gorbach et al. | |

* cited by examiner

APPARATUS AND METHOD FOR SHARING PERSONAL ELECTRONIC-DATA OF HEALTH

CROSS-REFERENCE TO RELATED APPLICATION(S)

This application claims the benefit under 35 U.S.C. § 119(a) of an Indonesian patent application filed on Dec. 18, 2015 in the Indonesian Patent Office and assigned Serial number P00201508592, and of a Korean patent application filed on May 26, 2016 in the Korean Intellectual Property Office and assigned Serial number 10-2016-0065074, the entire disclosure of each of which is hereby incorporated by reference.

TECHNICAL FIELD

The present disclosure relates to an apparatus and a method for sharing of electronic-data of health (e-health data). More particularly, the present disclosure relates to an apparatus and a method for storing and sharing e-health data in aspects of protection of personal privacy.

BACKGROUND

Medical records are commonly created when health professionals treat patients. Today, most health institutions usually save the records in their database for patient further treatments. It may comprise of various personal records, such as patient or family medical history, lifestyle details, laboratory test results, surgery record, and even genetic testing result. However, by the development of ubiquitous and pervasive computing, now medical records are no longer created only by health professionals. The emerging of health sensors on mobile device, such as pulse and oxygen in blood sensor, airflow sensor, body temperature sensor, electrocardiogram sensor, and the like, enable people to independently check their health and record their own data in device.

Even though the technology is still in progress towards personal future health system, it is important to understand privacy aspect on medical records. Moreover, the future e-health system will be more likely to enable people to manage their medical records that are created by health institution. Authorization for accessing and having the records is crucial to consider as patient's privacy since the records can be possibly used by unauthorized parties to trade in return for things such as insurance coverage, employment opportunities, government benefits, and safety investigation. Therefore, this disclosure discloses the system and a method for trust management in personal e-health to manage trust between patient and second party in sharing medical records in dynamic and un-trusted environment.

The above information is presented as background information only to assist with an understanding of the present disclosure. No determination has been made, and no assertion is made, as to whether any of the above might be applicable as prior art with regard to the present disclosure.

SUMMARY

Aspects of the present disclosure are to address at least the above-mentioned problems and/or disadvantages and to provide at least the advantages described below. Accordingly, an aspect of the present disclosure is to provide an apparatus and a method for sharing of electronic—data of health (e-health data).

Another aspect of the present disclosure is to provide a secure apparatus and a method for a trustor to maintain the confidentiality of e-health data by using a biometric encryption key for identity (ID) verification.

Another aspect of the present disclosure is to provide an apparatus and a method for controlling that only a desired trustee could request an access permit to trustor's e-health data by using trustee system.

Another aspect of the present disclosure is to provide an apparatus and a method that works independently without requiring any direct intervention of the parties to send or receive the e-health data, or to verifying the ID of e-health data owner.

Another aspect of the present disclosure is to provide an apparatus and a method whereas e-health data owner can choose and create their own security pattern to encrypt the data, hence only the e-health data owner shall be able to access. This security pattern is not limited to create one pattern only, but various patterns instead according to owner's requirement In accordance with an aspect of the present disclosure, an operation method of an electronic device for sharing data of health is provided. The operation method includes creating a security policy in accordance with at least one input of a user of the electronic device through a security policy design tool, creating a link for gaining access to the health data based on the security policy, receiving a health data transmission request that is transmitted using the link from a health data request device, and performing authentication on the transmission request based on the security policy.

In accordance with another aspect of the present disclosure, an electronic device for sharing data of health is provided. The electronic device includes a communication unit configured to perform communication with a health data request device, and a control unit configured to control the communication unit. The control unit creates a security policy in accordance with at least one input of a user of the electronic device through a security policy design tool, and generates a link for gaining access to the data of health based on the security policy. The communication unit receives a transmission request for the data of health that is transmitted using the link from the health data request device. The control unit performs authentication on the transmission request based on the security policy.

In accordance with another aspect of the present disclosure, an electronic device requesting data in a network for sharing data of health is provided. The electronic device includes a communication unit configured to perform communication with a health data share device, and a control unit configured to control the communication unit. The communication unit transmits a transmission request for the data of health to the health data share device, using a link that is created based on a security policy in the health data share device, and receives a request for performing authentication on the transmission request from the health data share device, and after receiving the authentication request, requests a security ID, and receives the security ID, and transmits a request for transmission of the data of health to the health data share device by using the security ID, and receives the requested data based on the security policy.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
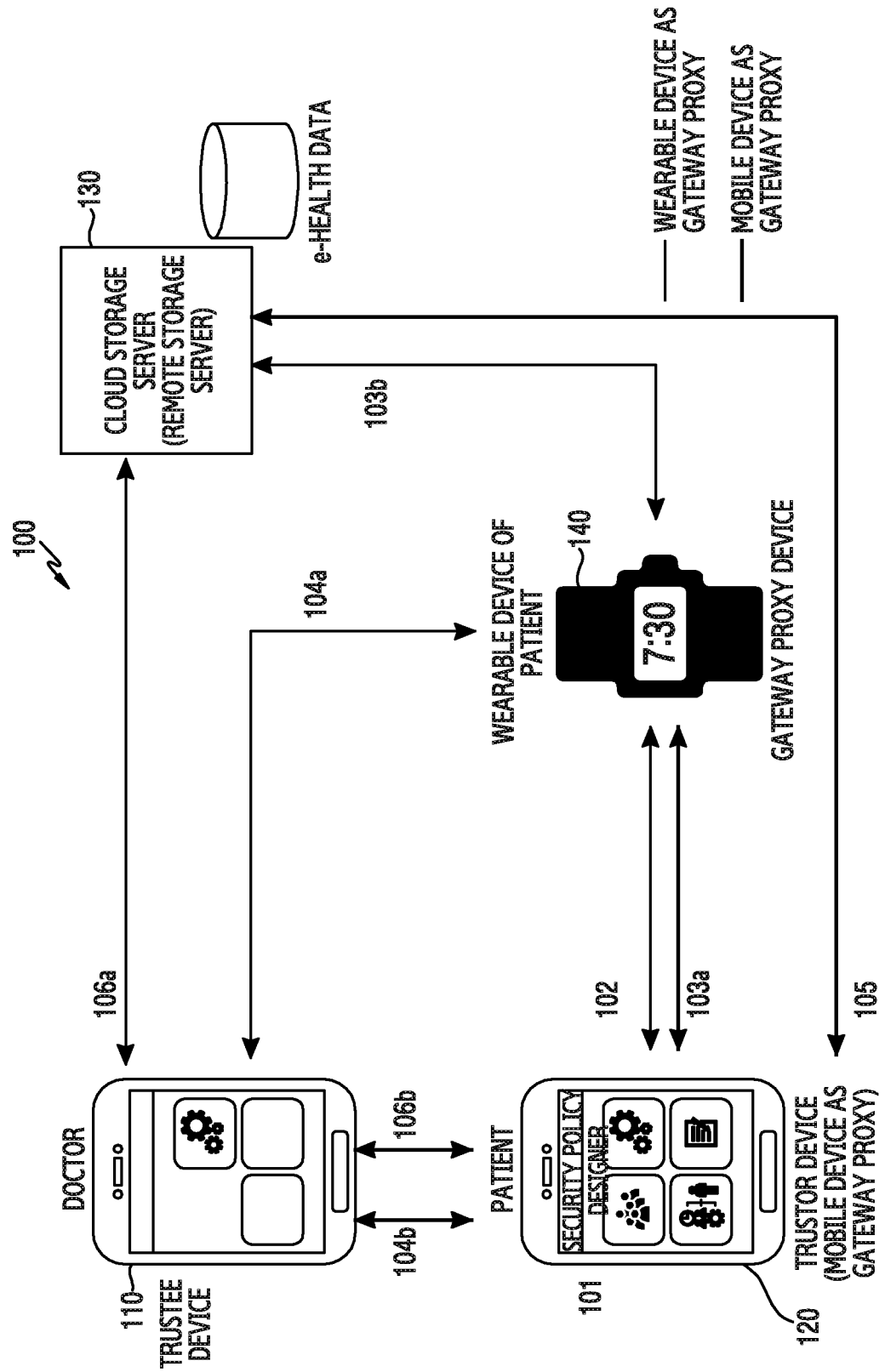
FIG. 1 is a general overview of a trust management system in storing and transferring personal electronic—data of health (e-health data) according to an embodiment of the present disclosure.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

The terms used herein including the technological or scientific terms can have the same meaning as those commonly understood by a person having ordinary knowledge in the art mentioned in the present disclosure. Among the terms used in the present disclosure, the terms defined in a general dictionary can be interpreted as the same or similar meanings as the contextual meanings of a related technology, and are not interpreted as ideal or excessively formal meanings unless defined clearly in the present disclosure. According to cases, even the terms defined in the present disclosure cannot be interpreted to exclude various embodiments of the present disclosure.

Various embodiments of the present disclosure described below explain a hardware access method, for example. However, the various embodiments of the present disclosure include a technology using all hardware and software and therefore, it is not that the various embodiments of the present disclosure exclude a software based access method.

This disclosure proposes a trust management system for storing and sharing personal electronic—data of health (e-health data) securely in insecure environment. The trust management system is responsible in evaluating and determining access rights for trustee, and also provide flexibility for user to store their personal health data locally in their own personal mobile devices (e.g., smart phones, tablets, and the like) or remotely in the cloud storage.

In this disclosure, users can design and manage security policy templates from their own personal mobile device via security policy designer tool by combining user role scheme and signed with user's biometric data. Thereafter, using user's personal mobile device, gateway proxy will distribute trustor's user identity (ID) to other people and responsible as the ID authorization to validate user's ID. Once user's ID is verified, trustee will be automatically granted access rights to view trustor's e-health data securely. With the trust management system, patient's health data will be saved with encryption mechanism and then store them to local and/or remote storage. These processes run through custom protocol on the top of personal wireless networks.

This disclosure will build a trust management system to preserve user's privacy and secure health data acquired from personal health sensor devices which can be shared and stored in an insecure environment either in local or remote storage. The trust management system comprises of: 1) an authentication handshake procedure which uses secret hidden handshake based machine-to-machine (M2M) communication by involving local network, mobile device and wearable device as local authority, and 2) personal security policy builder on smart devices added with biometric data (i.e. iris, fingerprint or a form of face), which utilizes biometric attributes-based. This security policy designer will enable trustor to create personalized and customized trust security policy for each different trustee.

To be able to send the e-health data, trustor should first match the prearranged biometric encryption. After unlocking the encryption, trustor will receive a token in the form of a secure Link to subsequently be shared to trustee. Further, when trustee access the link on smart devices or similar kind of electronic devices, the link will automatically request to download the trustee system which is a system that is installed on trustee's device which shall functions as a secure communication media to transfer e-health data to trustor. After downloaded, the system will request confirmation for trustor's ID and asks trustor to transfer the e-health data. To be able to answer the request, trustor will too be requested to do the biometric authentication prior to e-health data transfer. Before do the above process, trustor could set the expiration time period of the e-health data through the security policy designer, to allow trustor to control the e-health data that has been transferred to other parties.

The present disclosure relates generally to a trust management system in providing secure communications for storing and sharing personal e-health data in an insecure environment either in local or remote storage, with an authentication handshake procedure which utilizes biometric attribute-based and multi-platform trust-based communication gateway to preserve user's privacy.

This disclosure has five features, which are better than scheme of the related art, to wit:

Firstly, the present disclosure is based on a reliable security (trust management) to store and transfer the e-health data, by:

Using a security policy designer whereas e-health data owner can chose and create their own customized security patterns to limit unauthorized parties from accessing and transferring their personal e-health data. The security policy designer allows trustor to create more than one security pattern to enable trustor in applying different kind of pattern to each different trustees;

This security pattern combines variety of role schemes which are intended for trustee and trustor's biometric data;

Using biometric verification to encrypt the e-health data which functions to protect data which stored locally on smart device or stored remotely at a server. This biometric verification is enable trustor to set the encryption by more than one feature, to wit face, fingerprint or eyeprint.

Secondly, the present disclosure arranges online data transaction securely by trust management protocol, by:

protecting user's privacy by applying trust-based cross-platform communication to do the verification performed by local network and user's device which act as local authorization provider without any involvement of third party required.

applying communication between machines (M2M) from trustor's to trustee's smart device by implementing the secret-handshake-based background process.

FIG. 1 is a general overview of a trust management system in storing and transferring personal e-health data according to an embodiment of the present disclosure.

Referring to FIG. 1, a trust management system 100 comprises a trustee device 110, a trustor device 120, a cloud storage server (remote storage server) 130, and a gateway proxy device 140. A patient who already has a collection of digital health data as a result of self-measurement using personal health devices would like to share the data with the doctor by still preserving patient's privacy with restricted data and accessibility.

First, a patient will measure one's own health through personal health sensor devices. Thereafter, patient can build customized policy templates using security policy designer tools to be shared with a doctor or a group of people. A security policy designer tool will enable patients to create different policy templates to be shared with different people. Further, if a doctor (trustee), requests e-health data from a patient (trust-provider/trustor), patient will give a token such as a link in this sample scenario, which doctor can open it via a browser from any devices, such as mobile devices, tablets, personal computer (PC), and the like. Herein, the token is a unique address code to access a system, and can be anything used as a unique address code, such as uniform resource locator (URL), barcode, quick response (QR) code or secret string. Once the patient grants access rights to a doctor to access patient's data, doctor will be asked to open a trustee system, which can be installed or preloaded in the smart device, from the patient.

This trustee system includes a security policy with specific purpose and context, which means only health related data, will be exchanged through this client app. Furthermore, a temporary ID of the patient will be generated from secure keys including a security policy that is secured and free of Virus, Trojan, or Malware.

After obtaining a verified access rights, the doctor can finally retrieve personal data from the patient's local storage or remote server and view patient's personal health data in a secured environment. Encryption method is applied to preserve and secure user's data. With this trust management system, client app will be uninstalled automatically after being unused or based on certain time limit defined in security policy templates.

Referring to FIG. 1, in operation 101, the patient can build the customized security policy for its own personal doctor by using the security policy designer tool in the trustor device 120. In operation 102, the patient measures a health state through the gateway proxy device 140 that is a personal health sensor device. In operation 103a, the patient saves e-health data in a local storage device of the trustor device 120 in accordance with an encryption mechanism. In operation 103b, the patient saves the e-health data in the cloud storage server 130 in accordance with the encryption mechanism. In operation 104a, the patient grants temporary access rights for the e-health data through the gateway proxy device 140, and the doctor installs a security client application to make a request for resources. In addition, in operation 104b, the patient grants temporary access rights for the e-health data through the trustor device 120 that is a gateway proxy, and the doctor installs the security client application to make a request for resources. In operation 105, the trustor device

120 performs an ID verification role, and performs authentication for transmitting the e-health data from the local/cloud storage device to the doctor. In operation 106a, the cloud storage server 130 transmits the secured data to the trustee device 110. In addition, in operation 106b, the local storage device of the trustor device 120 transmits the secured data to the trustee device 110. In addition, in operation 105, the local storage device of the trustor device 120 transmits the secured data to the cloud storage server 130.

Figure 2:
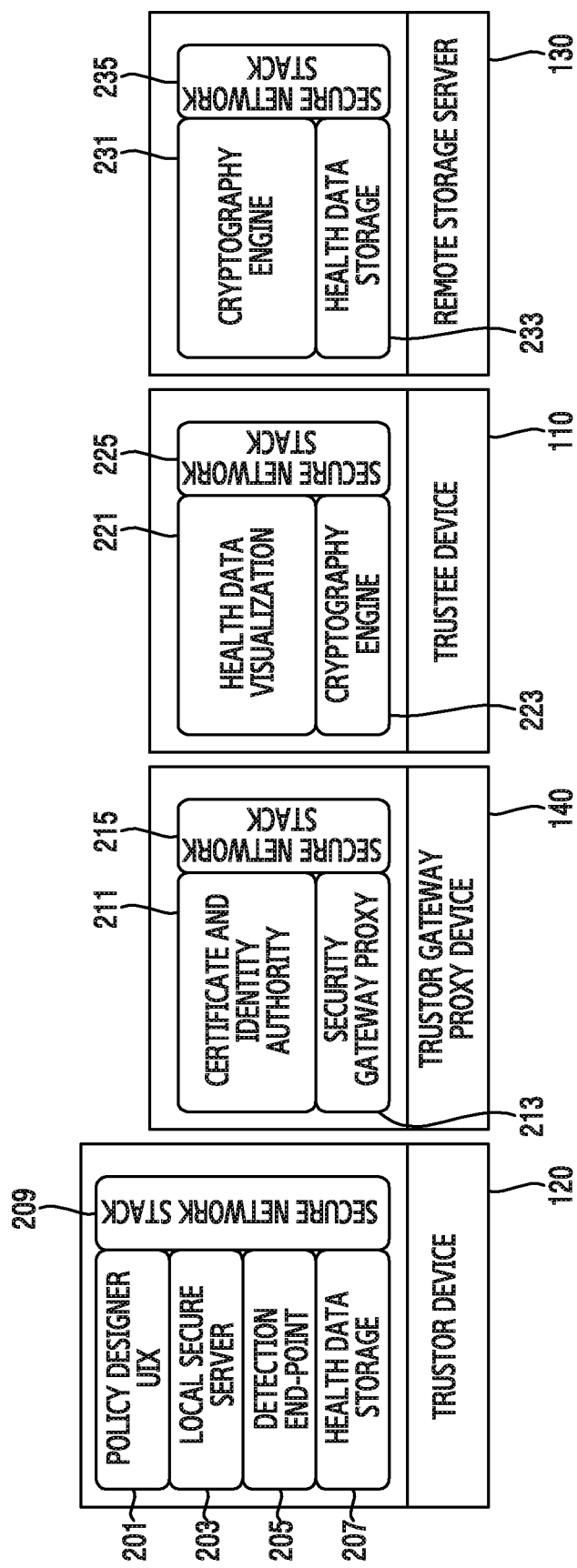
FIG. 2 is a general design of a trust management component system according to an embodiment of the present disclosure.

FIG. 2 is a general design of a trust management component system according to an embodiment of the present disclosure.

Referring to FIG. 2, the trustor device 120 is comprised of a policy designer user interface eXtensible Markup Language (XML) a User Interface XML (UIX) 201, a local secure server 203, a detection end-point 205, a health data storage 207 and a secure network stack 209. The trustor gateway proxy device 140 (or the trustor device 120 as the gateway proxy device) is comprised of a certificate and ID authority 211, a secure gateway proxy 213 and/or a secure network stack 215. The trustee device 110 is comprised of a health data visualization 221, a cryptography engine 223 and/or a secure network stack 225. The remote storage server 130 is comprised of a cryptography engine 231, a health data storage 233 and/or a secure network stack 235. Deployed components are distributed on trustor and trustee's devices. Each system entity consists of installed components that are used to communicate to other system entity. The following is a brief of system component for trust management system:

Policy designer UIX 201 is a tool to create personalized and customized and customized trust security policy by combining user role schemes and biometric data on certain context.

Local secure server 203 is personal health data, such as heart, blood and glucoses data that belongs to Trustor. These data are retrieved from health sensor devices.

Detection end-point 205 is a network end-point that receives health data from sensor devices.

Health data storage 207 and 233 are common storages that have stored encrypted health data, such as heart, blood and glucoses data that belongs to Trustor.

Secure network stack 209 is a network stack library that is used to establish a secure communication included secret handshakes between trustor's device and trustee's device. Secure Network Stack 215, 225 and 235 are network stack libraries that are used to establish a secure communication included secret handshakes.

Certificate and ID authority 211 is a security module that is used to validate a certificate and an ID from trustor.

Secure gateway proxy 213 is a network app that is used a bridge between trustor's devices and trustee's devices. This module communicates to another system entity through secure network stack.

Health data visualization 221 is a UI module that is used to show health data from trustor.

Cryptography engine 223 and 231 are cryptography libraries that are used to encrypt and decrypt with trustor's credential ID.

Figure 3:
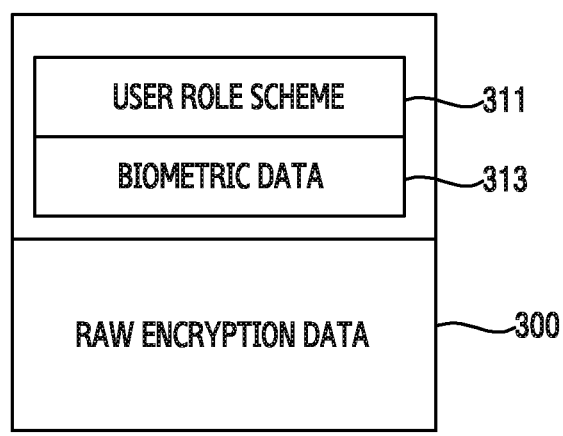
FIG. 3 is a structure of a trust model component for data encryption system according to an embodiment of the present disclosure.

FIG. 3 is a structure of a trust model component for data encryption system according to an embodiment of the present disclosure.

Referring to FIG. 3, a trust model 300 consists of a user role scheme 311 and biometric data 313. Furthermore, this model is encrypted using attribute-based encryption with customization. The encrypted data will be used as a token for requester to retrieve e-health data.

Figure 4:
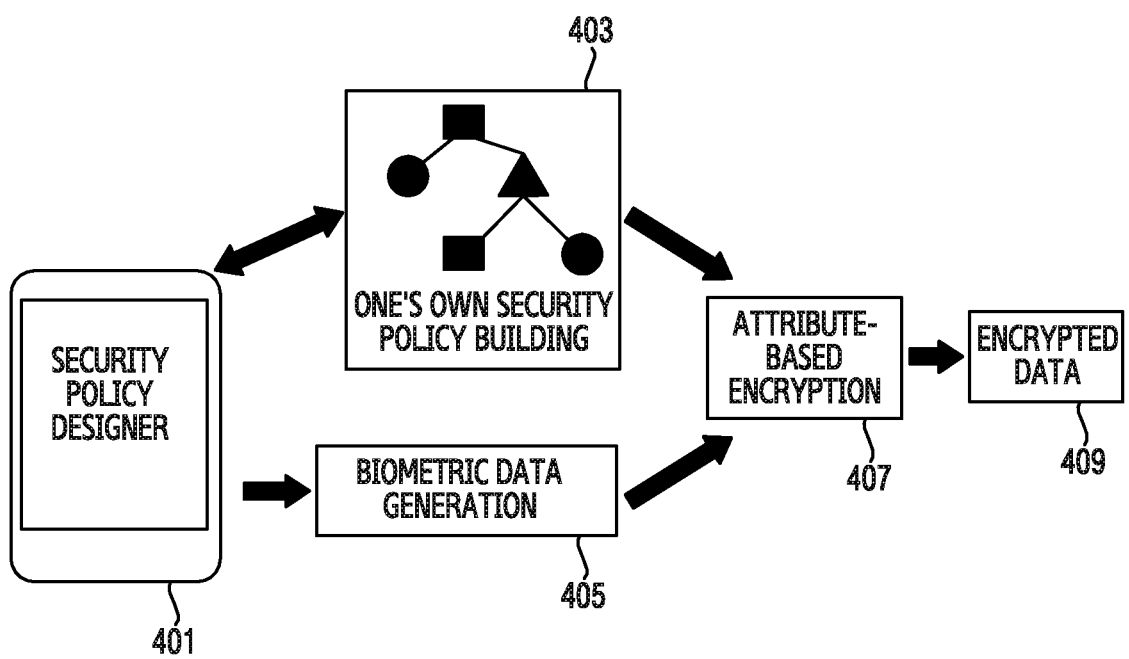
FIG. 4 is a flow diagram for generating a trust model object according to an embodiment of the present disclosure.

FIG. 4 is a flow diagram for generating a trust model object according to an embodiment of the present disclosure.

Referring to FIG. 4, a user generates a trust object for an access right by combining user role scheme and biometric data using security policy designer tool via user's personal smart devices such as mobile devices, tablets, and the like.

Referring to FIG. 4, first, in operation 401, a trustor executes the security policy designer tool. In operation 403, the trustor builds a security policy through the security policy designer tool. In operation 405, the trustor creates the biometric data. In operation 407, the trustor performs attribute based encryption by combining the user role scheme in the previous operation and the biometric data. Thereafter, in operation 409, the trustor creates a trust object for access rights for finally encrypted data.

Figure 5:
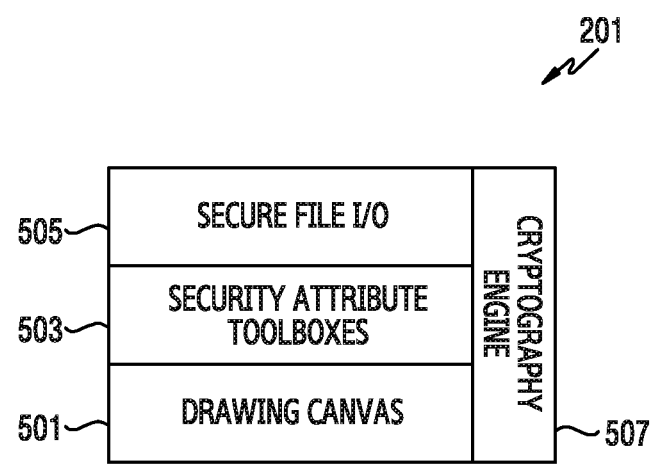
FIG. 5 is a general structure for a component of a security policy designer User Interface eXtensible Markup Language (UIX) according to an embodiment of the present disclosure.

FIG. 5 is a general structure for a component of a security policy designer UIX according to an embodiment of the present disclosure.

Referring to FIG. 5, the policy designer UIX 201 is comprised of a drawing canvas 501, security attribute toolboxes 503, a secure file input/output (I/O) 505 and/or a cryptography engine 507. User can customize several kind of security policy by using a smart device. The security policy will be created using security policy designer UIX 201. The following is a brief of component of security policy designer UIX 201 which is shown in FIG. 5:

Drawing canvas 501 is a graphical user interface (GUI) presentation which is used to build a policy by drawing. Users can put security attributes toolbox items on this canvas.

Security attribute toolboxes 503 is a list of security attribute components, such as smart device, group role, expired date time or custom attributes. These toolboxes include "AND", "OR" attributes.

Secure file I/O 505 is a file module to manage file I/O such as file format, reading and writing.

Cryptography engine 507 a cryptography library that is used to encrypt and decrypt with trustor's credential ID.

Figure 6:
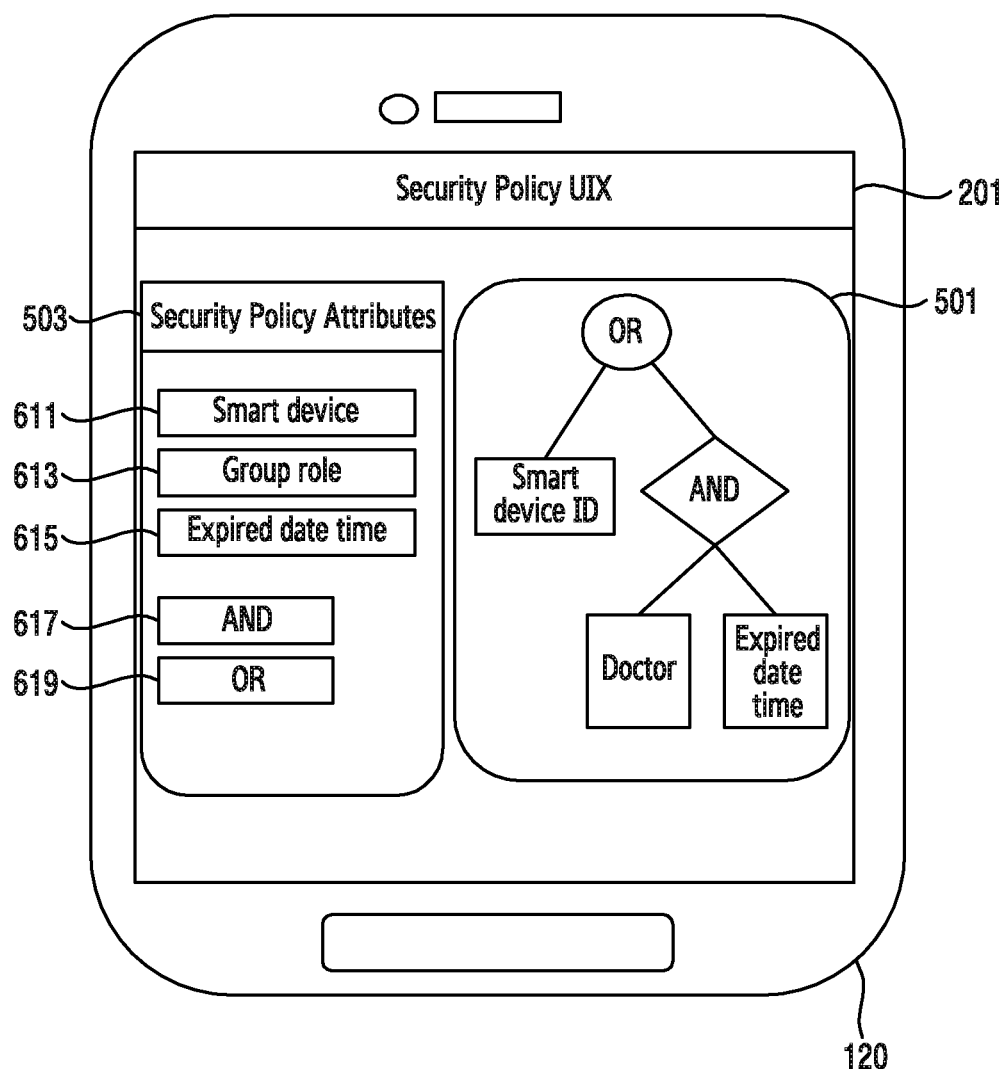
FIG. 6 is a scheme of a component of a security policy designer UIX in a trustor device according to an embodiment of the present disclosure.

FIG. 6 is a scheme of a component of a security policy designer UIX in a trustor device according to an embodiment of the present disclosure.

Referring to FIG. 6, the security policy designer UIX 201 is comprised of the security attribute toolboxes 503 and the drawing canvas 501. In addition, the security attribute toolboxes 503 include security attributes, such as a smart device 611, a group role 613, an expired date time 615, and the like, and "AND" 617 and "OR" 619 attributes. Security policy consists of the combination "AND" and "OR" attributes which can be applied to a certain context. This tool will also generate public and private keys. Furthermore, security policy attribute object is integrated with user's biometric data such as face, iris or fingerprint. Thereafter, it will be encrypted using attribute-based encryption method.

Figure 7:
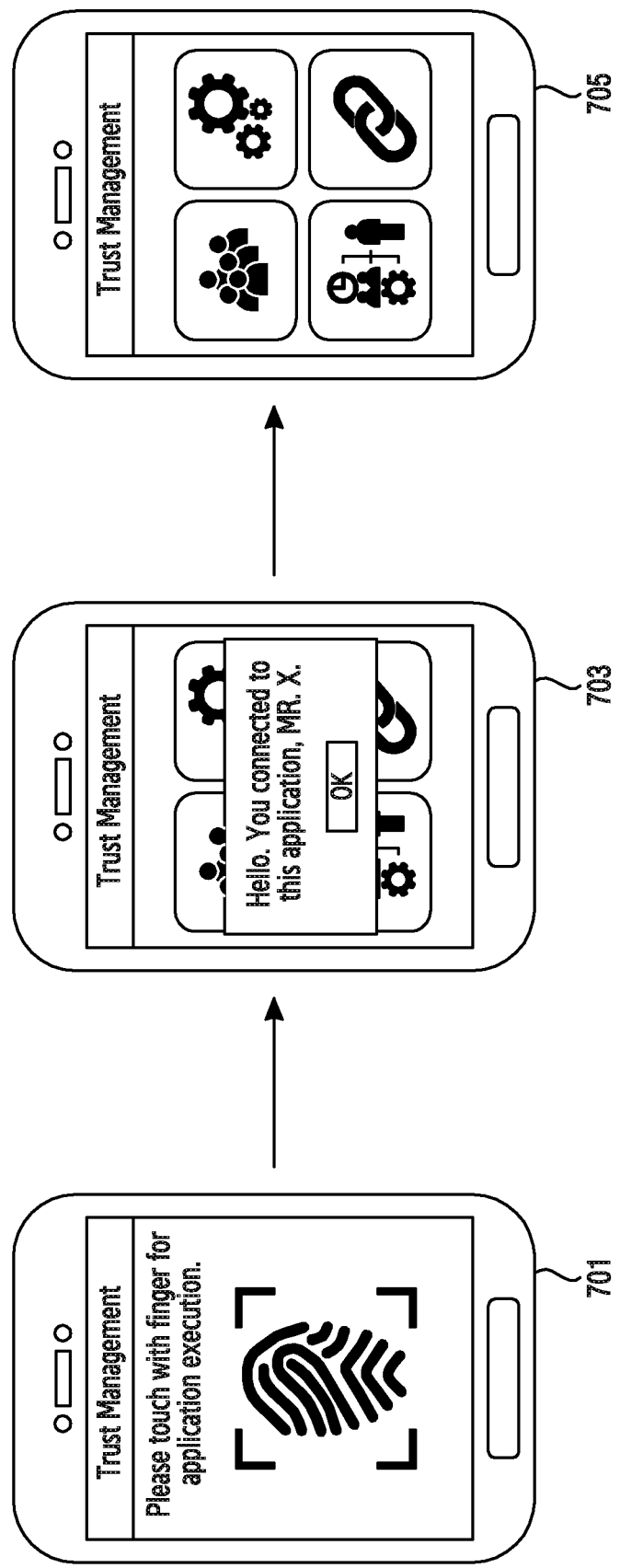
FIG. 7 is a sample scenario of a user interface (UI) in opening a security policy designer UIX that requires biometric authentication according to an embodiment of the present disclosure.

FIG. 7 is a sample scenario of a user interface (UI) in opening a security policy designer UIX that requires biometric authentication according to an embodiment of the present disclosure.

Referring to FIG. 7, security policy designer UIX application is installed into smart devices to enable users to design and manage security policy templates. Security policy UIX provides a toolbox which consists of "AND" and "OR" box to enable user to create a security policy template by combining "AND" or "OR" attributes. To open a security policy designer, trustor should do a biometric authentication.

In state 701, a screen for authentication is displayed. Through the screen such as state 701, a trustor device performs bio authentication for executing the security policy designer, for example, authentication through fingerprint recognition. In state 703, a message according to a success of the bio authentication is displayed. For example, if the bio authentication is successfully performed, the trustor device floats a message window according to the success of the bio authentication. In state 705, a screen for security policy design is displayed. For example, if the bio authentication is made successfully, the trustor device shows a basic screen including a security policy designer tool.

Figure 8:
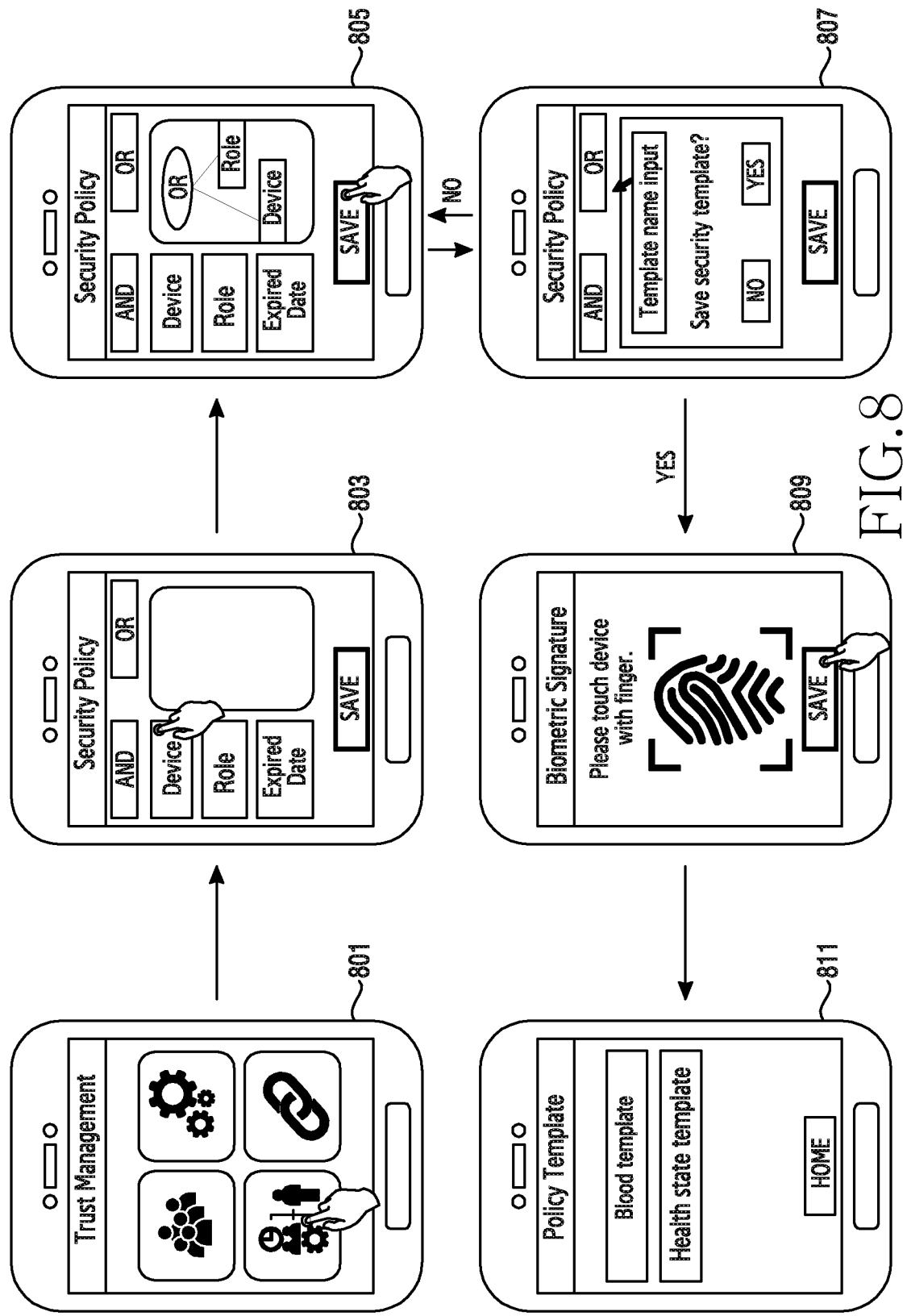
FIG. 8 is a sample scenario of a UI in creating a security policy according to an embodiment of the present disclosure.

FIG. 8 is a sample scenario of a UI in creating a security policy according to an embodiment of the present disclosure.

Referring to FIG. 8, to build a security policy template, user can click and drag from a security policy attributes toolbox. This toolbox provides several attributes which users can attach into their security policy template. For example, user can create security policy template by combining using "AND" and/or "OR" specified attributes such as smart device types (e.g., wearable, smart phone, tablets, and the like), group role (e.g., personal doctor, family, friends, and the like), time limitation (e.g., immediately expired after x minutes view, expired within 1-day, no expiration date, and the like) and other attributes. After a security policy template is created, this template will be signed by biometric signature to attain data integrity. To build a security policy, users do the following operations:

In state 801, a trustor device displays a basic screen of a trust management system. Through the screen such as state 801, a trustor executes a security policy designer.

In state 803, the trustor device displays a security policy designer UIX screen. Through the screen of state 803, the trustor selects a security attribute and creates a new security template.

In state 805, the trustor device displays a screen selecting and combining one or more items among the security attributes to build a security policy. The trustor builds the security policy by combining "AND" and/or "OR" attributes.

In state 807, the trustor device displays a message for storage after security policy designing. For example, if the trustor inputs a template name and clicks a button "Yes", the trustor device saves the security template.

In state 809, the trustor device displays a screen for the trustor to sign the created security policy with fingerprint. For example, the trustor can sign the security template by using biometric data of at least one of fingerprint, iris or face.

In state 811, the trustor device displays the created security policy template after the security policy is completed. For example, the trustor can create respectively different templates in accordance with the type of e-health data such as a blood template, a health state template, and the like.

The trustor distributes an ID and a security key to a trustee through the following additional operation.

Figure 9:
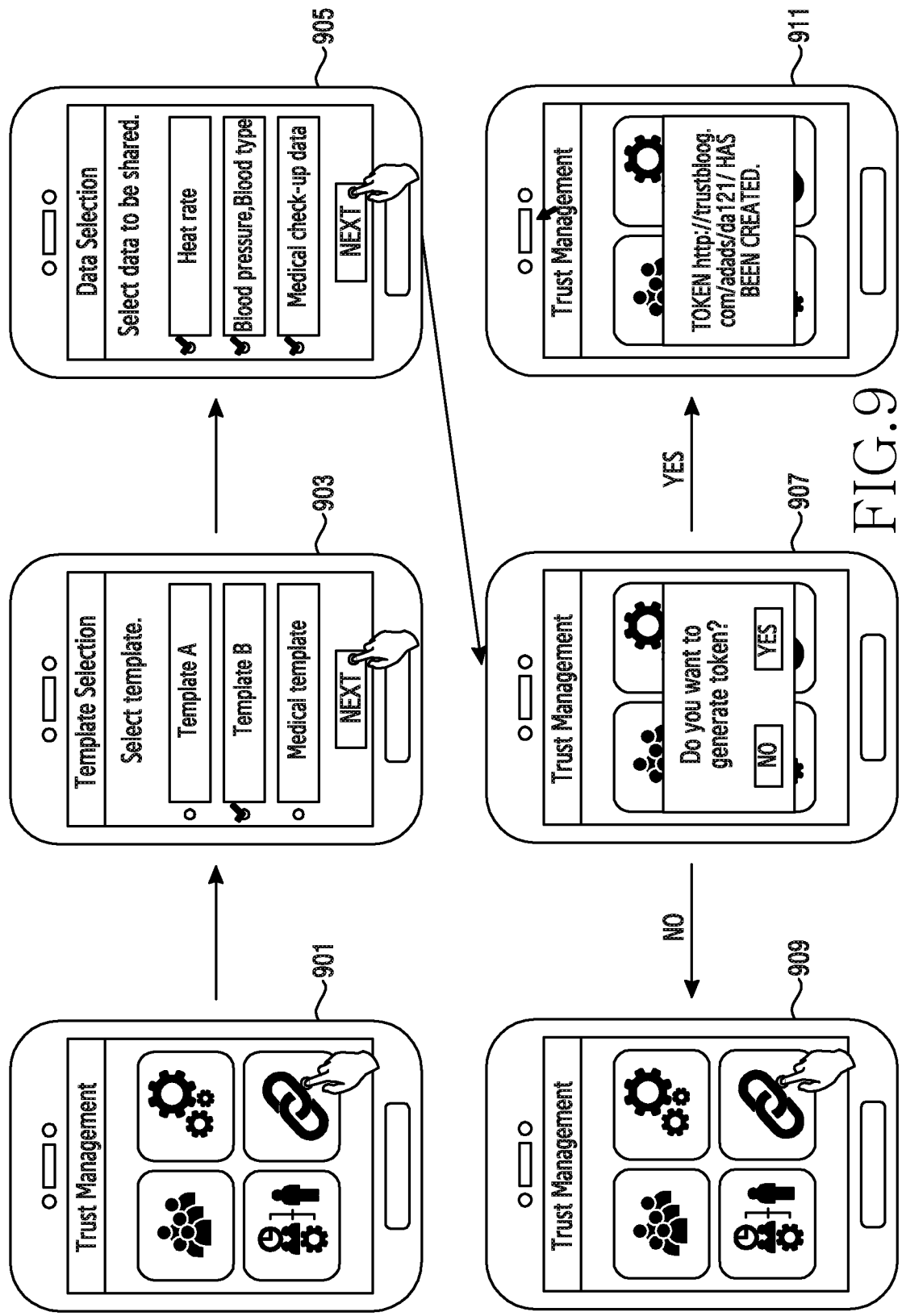
FIG. 9 is a sample scenario of a UI (a trustee's device) in generating a link as a token for a trustee in order to obtain e-health data according to an embodiment of the present disclosure.

FIG. 9 illustrates a sample scenario of a UI (a trustee's device) in generating a link as a token for a trustee in order to share e-health data according to an embodiment of the present disclosure.

Referring to FIG. 9, a process flow of creating the data sharing link for the trustee is given as follows.

In state 901, a trustor device displays a basic screen of a trust management application. Through the screen such as state 901, a trustor executes the trust management application.

In state 903, the trustor device displays a screen selecting several security policy templates. Through the screen of state 903, the trustor selects the security policy templates.

In state 905, the trustor device displays a screen selecting data to be shared. For example, the trustor selects one or more health data needing to be shared with the trustee among e-health data such as a heart rate, a blood pressure, a blood type, health check-up data, and the like.

In state 907, the trustor device displays a message for token creation after selecting the data to be shared. For example, the trustor creates a link enabling the trustee to gain access to the selected data (referring to FIG. 9). If the trustor selects "No" in state 907, the link creation is canceled and, in state 909, the trustor device again returns to the original basic screen. If the trustor selects "Yes" in state 907, in state 911, the trustor device displays a URL link of a created token. To perform this work, the trustor has to perform biometric authentication (referring to FIG. 7).

Thereafter, the trustee can acquire the created link from the trustor and, through the link, the trustee can gain access to the encrypted shared data.

Figure 10A:
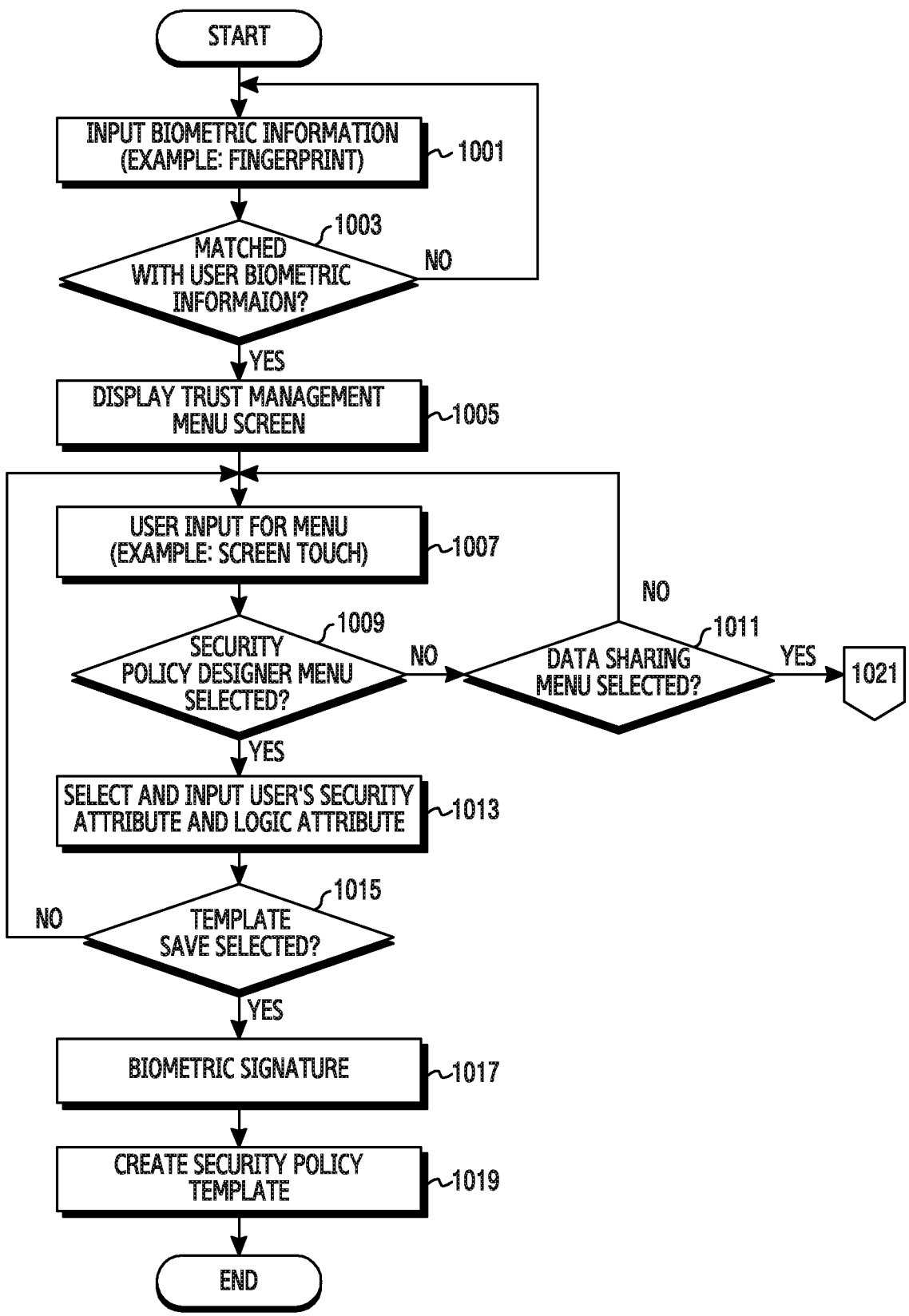
FIGS. 10A and 10B illustrate a flowchart of creating a security policy and an access link in a trustor device according to an embodiment of the present disclosure.
Figure 10B:
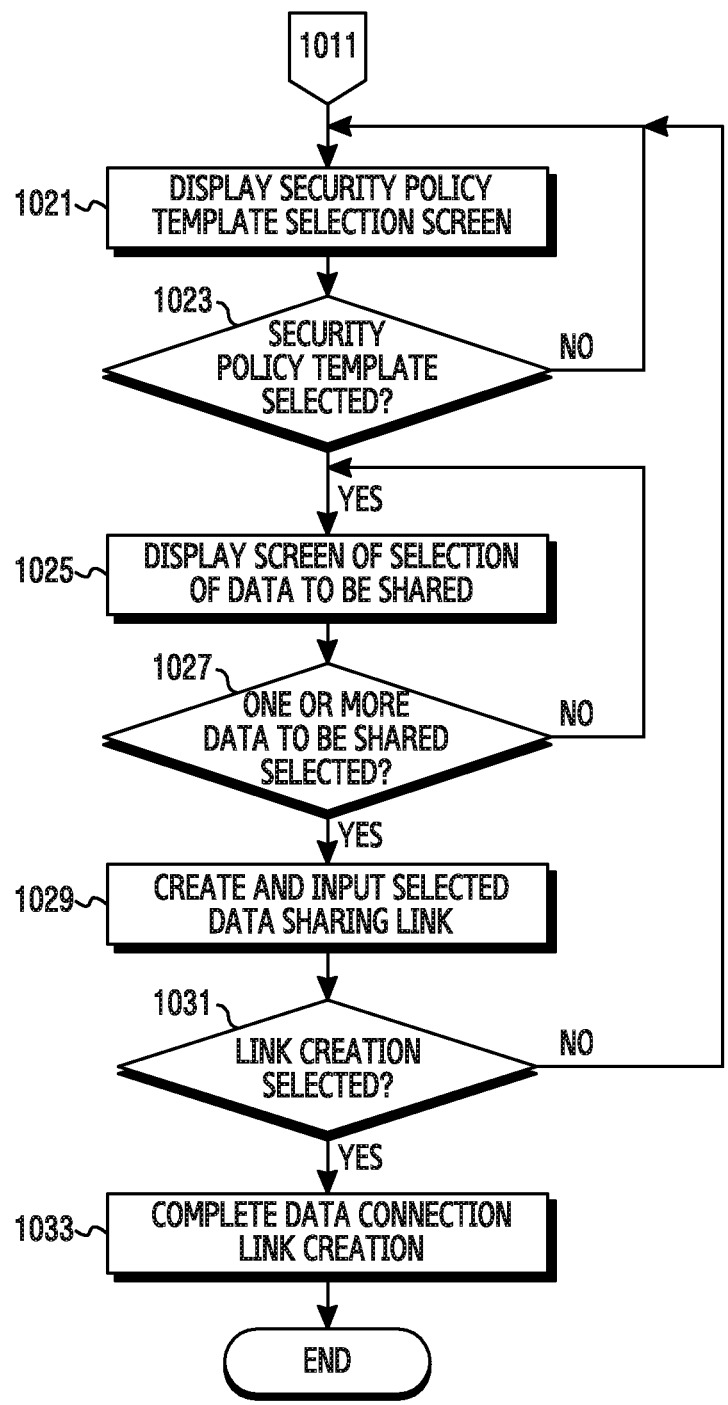

FIGS. 10A and 10B illustrate a flowchart of creating a security policy and an access link in a trustor device according to an embodiment of the present disclosure.

Referring to FIGS. 10A and 10B, a flow of a process of building the security policy for a trustee and creating the link accessible to data to be shared in the trustor device is given as follows.

In operation 1001, the trustor device gets an input of user's biometric information for the sake of trust management system execution. For example, the biometric information can be any one of information such as fingerprint, face, iris, and the like. Operation 1001 can be carried out through a screen getting an input of biometric information in a smart device, and the like, in which a trust management system is installed. In accordance with an embodiment, operation 1001 can be executed through the screen such as state 701 of FIG. 7.

In operation 1003, the trustor device determines if the inputted biometric information is matched with previously stored biometric information. For example, the trustor device determines if inputted fingerprint recognition information is matched with previously stored trustor's fingerprint recognition information. If the determination result is that information matched with the previously stored trustor's biometric information is inputted, the trustor device proceeds to operation 1005. In contrast, if it is determined that information not matched with the previously stored trustor's biometric information is inputted, the trustor device again gets an input of biometric information in operation 1001.

In operation 1005, the trustor device displays a trust management menu screen. In other words, if the information matched with the previously stored biometric information is inputted, the trustor device displays the trust management menu screen that includes menus such as a security policy designer, data sharing, and the like. In accordance with an embodiment, operation 1005 can be displayed through the screen such as state 705 of FIG. 7.

In operation 1007, the trustor device gets a user input for a screen menu. For example, the trustor device can get a motion input such as a screen touch, and the like, for a specific menu in the trust management menu screen. The user input can be even predefined any motion such as a screen touch, a motion approaching a screen, and the like. Operation 1007 can be executed through a screen displaying various menus of the trust management system. In accordance with an embodiment, operation 1007 can be executed in a form of getting an input of a user's screen touch through the screen such as state 801 of FIG. 8. In accordance with another embodiment, operation 1007 can be executed in a form of getting an input of a user's screen touch through the screen such as state 901 of FIG. 9.

In operation 1009, the trustor device determines if the user input is for selecting a security policy designer menu. For example, the trustor device determines if a user touches the screen and selects the security policy designer menu. If it is determined to select the security policy designer menu, the trustor device proceeds to operation 1013. If it is not determined to select the security policy designer menu, the trustor device proceeds to operation 1011.

If it is not determined that the user input is for selecting the security policy designer menu, in operation 1011 the trustor device determines if the user input is for selecting a data sharing menu. For example, the trustor device determines if the user touches the screen and selects a data sharing link creation menu. If the determination result is that the data sharing menu is selected, the trustor device proceeds to operation 1021. In contrast, if it is determined that even the data sharing menu is not selected, the trustor device returns to the trust management menu screen and again gets a user input for the screen menu. If one or more trust management menus exist further, the trustor device can further perform an additional operation of determining if other menus have been selected by user inputs.

In operation 1013, the trustor device gets an input of a combination of security attributes and logic attributes through a security policy designer screen. In other words, if the security policy designer menu is selected, the trustor device displays the security policy designer screen, and gets an input of a selection of user's security attributes and logic attributes for security policy building. The security attributes can include at least one of a smart device, a group role, an expired date time or a client attribute, and the like. The logic attributes include at least one of "AND" and "OR" attributes. Operation 1013 can be executed through a screen displaying various security attribute and logic attribute toolboxes of the security policy designer tool. In accordance with an embodiment, operation 1013 can be executed in a form of getting an input of touching the user's attribute toolbox, and the like, or an input of dragging the attribute to a drawing canvas region, through the screens such as states 803 and 805 of FIG. 8.

In operation 1015, the trustor device determines if the user input is for selecting security policy template saving. For example, the trustor device determines if there has been a request for saving a new security policy template by the user input. If the determination result is that the template saving is selected, the trustor device proceeds to operation 1017. In contrast, if not saving the template is selected, the trustor device again returns to the trust management menu screen and gets a user input for the screen menu. Through a screen checking whether to save the security policy template, the user input of operation 1015 can be executed. In accordance with an embodiment, operation 1015 can be executed in a form of getting an input of a user's screen touch through the screen such as state 807 of FIG. 8.

In operation 1017, the trustor device gets a user's biometric signature to save the security policy template. In other words, to securely apply a security policy built by a user to a trustee, the trustor device gets a user's biometric signature on the security policy template. Operation 1017 can be executed through a screen getting an input of the biometric signature. In accordance with an embodiment, operation 1017 can be executed in a form of getting an input of a user fingerprint, and the like, through the screen such as state 809 of FIG. 8.

In operation 1019, the trustor device creates a security policy template on which the biometric signature is completed. For example, the trustor device creates and saves the security policy template that is created through a combination of security attributes and logic attributes for the trustee by the user. The execution result of operation 1019 can be displayed through a security policy template creation result screen. In accordance with an embodiment, operation 1019 can display a name of the created security policy template through the screen such as state 811 of FIG. 8.

In operation 1021, the trustor device displays a security policy template selection screen. If the data sharing menu is selected in the preceding operation 1011, the trustor device displays a screen capable of selecting a previously created security policy template. If there is not the previously created security policy template, the trustor device can display a message of instructing to first make a security policy template. Operation 1021 can be executed through the screen displaying the previously created security policy templates. In accordance with an embodiment, operation 1021 can arrange at least one previously created security policy template through the screen such as state 903 of FIG. 9, and get a user input in a screen touch manner.

In operation 1023, the trustor device determines if the security policy template has been selected by a user input. At this time, the user input can be even predefined any motion such as a screen touch, a motion approaching a screen, and the like. If the determination result is that the security policy template is selected, the trustor device proceeds to operation 1025. In contrast, if no security policy template is selected, the trustor device keeps displaying the security policy template selection screen.

In operation 1025, the trustor device displays a screen selecting data to be shared regarding the selected security policy template. For example, the trustor device displays a screen capable of selecting health data to be shared with a trustee in compliance with a selected security polity. Operation 1025 can be executed through a screen displaying at least one data to be shared. In accordance with an embodiment, operation 1025 can arrange the data to be shared through the screen such as state 905 of FIG. 9, and get a user input in a screen touch mariner.

In operation 1027, the trustor device determines if at least one data to be shared has been selected. The data to be shared in compliance with one or more security policies can be selected, and the trustor device determines if at least one data to be shared in compliance with the selected security policy has been selected. If at least one data is selected, the trustor device proceeds to operation 1029. In contrast, if no data to be shared is selected, the trustor device again displays the screen selecting data to be shared.

In operation 1029, the trustor device gets a user input for link creation for sharing the selected data. For example, to securely share the data to be shared in compliance with the selected security policy, the trustor device gets a user input for creating a link that shall be used for requesting access to the data. At this time, the trustee can gain access to the data to be shared only through the link in compliance with the security policy. The link can be a proper address code such as a barcode, a QR code or a secret string, and the like. In addition, the link corresponds to at least one of the type of accessible health data that is selected in compliance with the security policy, a sharing target of the health data and/or a sharing period of the health data. Operation 1029 can be executed through the screen getting a user input for link creation. In accordance with an embodiment, operation 1029 can inquire whether to create a link for data to be shared through the screen such as state 907 of FIG. 9, and get a user input in a screen touch manner.

In operation 1031, the trustor device determines if the link creation has been selected by a user input. In other words, the trustor device determines if a menu for creation of a link accessible to data to be shared has been selected by the user input. If the determination result is that the link creation is selected, the trustor device proceeds to operation 1033. In contrast, if the link creation has not been selected, the trustor device again displays the screen selecting the security policy template of operation 1021.

In operation 1033, the trustor device creates the link that is accessible to the data to be shared. For example, the trustor device creates the link that is accessible to the data to be shared in compliance with the security policy. When the trustor device creates the link accessible to the data to be shared, additional bio authentication can be performed. In a process of creating the access link, the data to be shared through the link can be encrypted combining the security policy and the biometric information. The execution result of operation 1033 can be displayed through an accessible link creation result screen. In accordance with an embodiment, operation 1033 can display address information of the created link, through the screen such as state 911 of FIG. 9.

Figure 11:
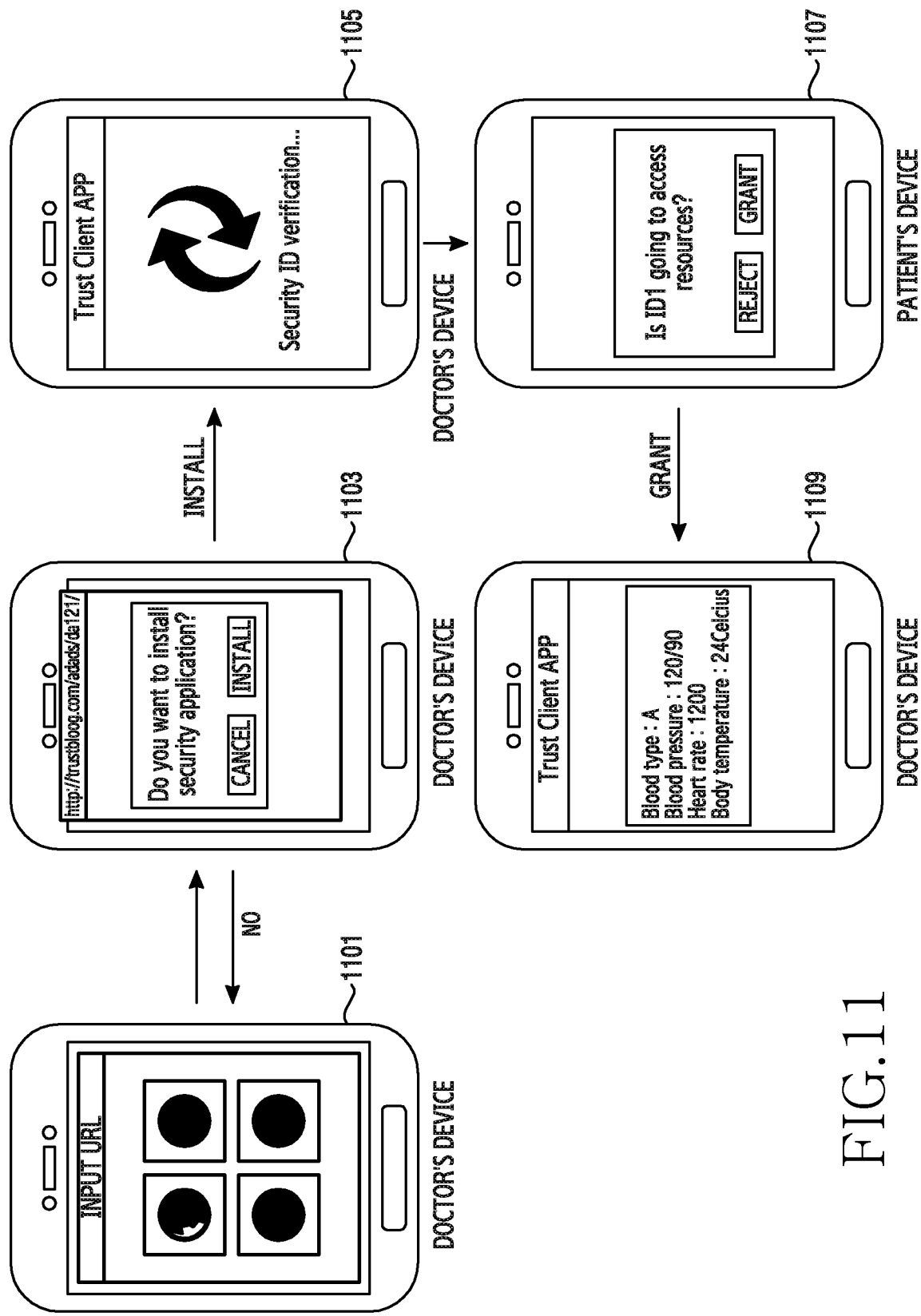
FIG. 11 is a sample scenario of a UI (a trustor's & trustee's device) in transferring and obtaining e-health data according to an embodiment of the present disclosure.

FIG. 11 illustrates a sample scenario of a UI (a trustor's trustee's device) in transferring and obtaining e-health data according to an embodiment of the present disclosure.

Referring to FIG. 11, a process flow between a trustor and a trustee is given as below.

In state 1101, a trustee device displays a screen inputting a URL address. Through the screen such as state 1101, a trustee shall input a link to a browser of the trustee device.

In state 1103, the trustee device displays a message for installation of a security client application. For example, the trustee device shall get a request for installation of the security client application through the browser. At this time, the security client application installation request can be transmitted from a gateway proxy or a trustor device.

In state 1105, the trustee device displays a screen verifying a security ID. For example, while the trustee device displays the screen such as state 1105 after the installation of the security client application, the trustee device shall send a request for a trustor's ID to the gateway proxy of the trustor device such as a wearable device through the security client application. Data exchange can use an encrypted java script object notation (JSON) form.

In state 1107, the trustor device displays a message responsive to the trustee's request. For example, after acquiring the trustor's ID, the trustee device sends an e-health data search request to the trustor device through the security client application. The data request from the trustee device is comprised of a request instruction and a trustor's ID. The trustor device accepts the request of the trustee. The trustor shall be able to verify the request of the trustee through authentication making use of a biometric signature.

If the verification is completed, in state 1109, the trustee device displays received e-health data. For example, a response to the request of the trustee shall be transmitted to the trustee with including the e-health data. Through the screen such as state 1109, the trustee device securely displays the e-health data. In accordance with an embodiment, if the verification is completed, the trustee device can receive and display decoded data. In accordance with another embodiment, the trustee device receiving the encrypted data after the verification is completed can perform a process of decoding the received data, and display the decoded data.

Figure 12:
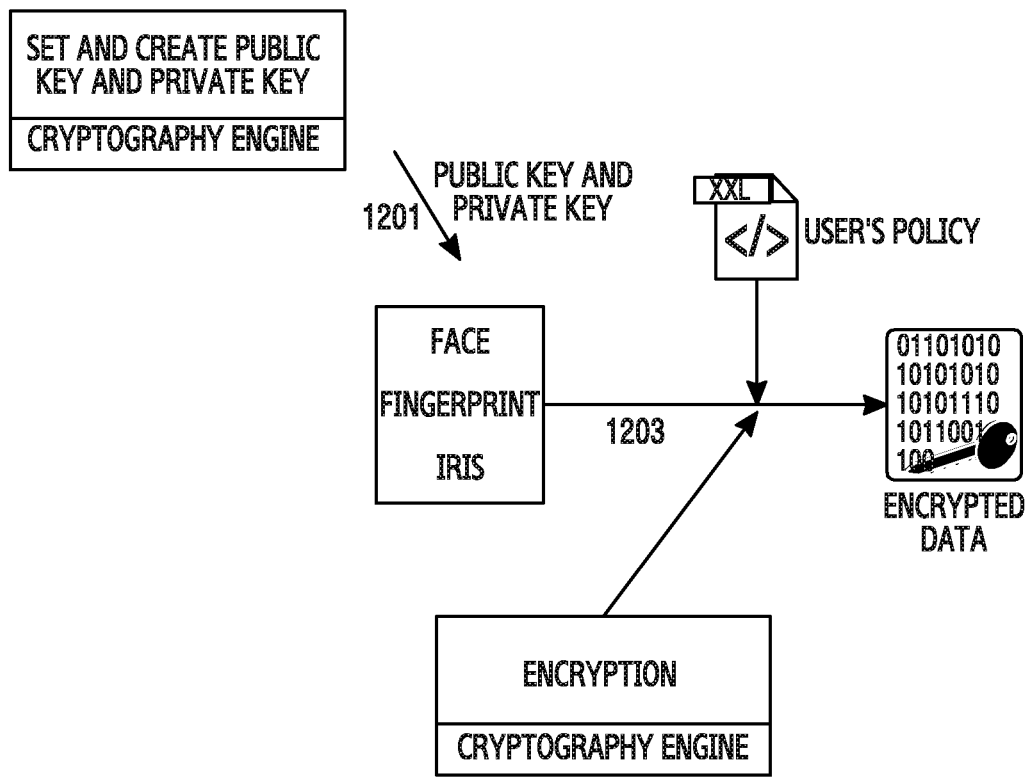
FIG. 12 is a flow diagram of a biometric-based encryption process for e-health data according to an embodiment of the present disclosure.

FIG. 12 is a flow diagram of a biometric-based encryption process for e-health data according to an embodiment of the present disclosure.

Referring to FIG. 12, personal data can be stored in local or remote storage. In the present disclosure, proposed a cryptography approach based on attribute encryption. The encrypted data shall consist of user's role scheme policy and biometric data to maintain the right access to the e-health data.

In operation 1201, a public key and a private key are created. In operation 1203, biometric data and a user's policy are combined to create encrypted data based on attribute encryption.

Figure 13:
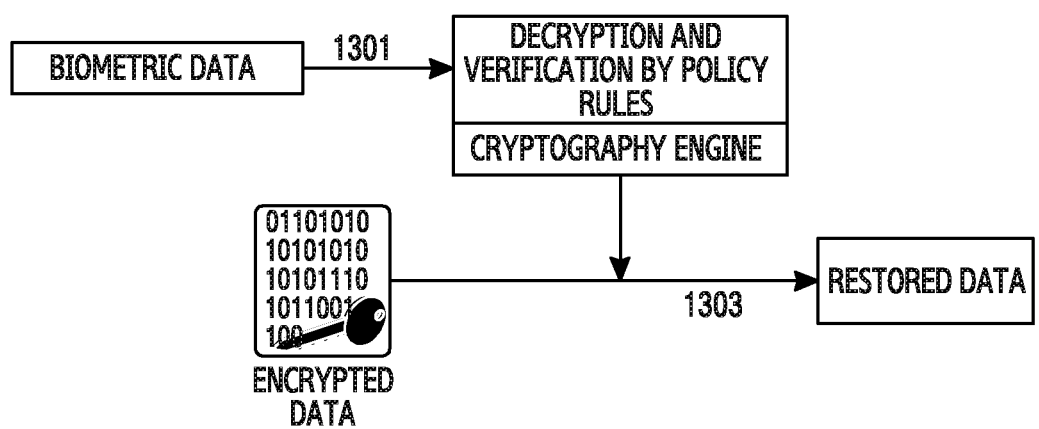
FIG. 13 is a flow diagram of a decryption process to restore e-health data into no password according to an embodiment of the present disclosure.

FIG. 13 is a flow diagram of a decryption process to restore e-health data into passwordless according to an embodiment of the present disclosure.

Referring to FIG. 13, in operation 1301, users should send biometric data for verification to decrypt data. In operation 1303, the system will check the security policy that is embedded in e-health data. If the biometric password does not match the security policy rules, thus e-health data will not be decrypted. Instead, the data will be opened if all safety requirements are met.

Figure 14:
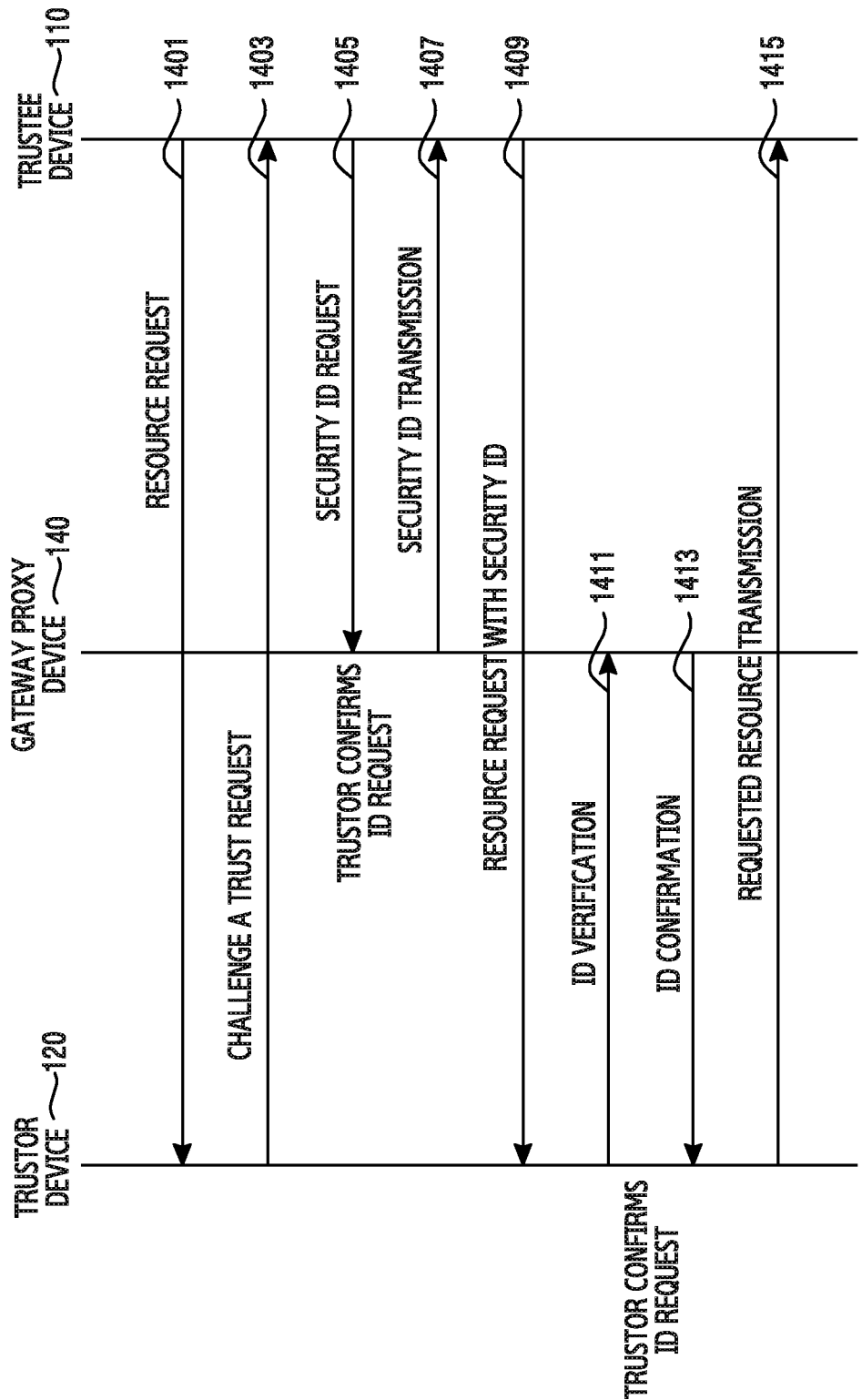
FIG. 14 is a flow diagram of an access control system using trust management protocol for e-health data transferring according to an embodiment of the present disclosure.

FIG. 14 is a flow diagram of an access control system using trust management protocol for e-health data transferring according to an embodiment of the present disclosure.

Referring to FIG. 14, a system and a method for providing an effective and secure method in giving access to resource on personal health system is proposed. The general access control flow in the proposed trust management system is described FIG. 14. FIG. 14 exemplifies a process in which the trustee device 110 sends a request for e-health data to the trustor device 120 in a state in which a security client application has been already installed in the trustee device 110. If it is a state in which the security client application is not installed in the trustee device 110, the trustee device 110 shall get a request for installation of the security client application from the trustor device 120 or the gateway proxy device 140.

In the present disclosure, a method that is effective and safe in giving access of data in the private health system is provided. This disclosure uses the term of "trustee" as the person making the request to access the e-health data, and term of "trustor" as a person who grant access to one's own e-health data. Conceptually, FIG. 14 describes the procedure by the time the trustee device 110 needs data from the trustor device 120. Furthermore, the proxy system (e.g., gateway proxy device 140) between the trustor device 120 and trustee device 110 intended to prevent direct communication between them to maintain trustor's privacy and build verification systems that are valid and safe.

The proxy system can be embedded into a. smart device or trustor's wearable device. The system is also equipped with the trustee system to maintain privacy by the time of data transaction. The first process performed is authentication between the trustee device 110 and trustor device 120 through the proxy system. The authentication process will produce a secure ID that cannot be cloned. By this ID, trustee device 110 will request the e-health data owns by trustor device 120. Trustor device 120 will verify the ID through a proxy system, If the ID is verified, trustor device 120 will grant the e-health data to trustee device 110.

Referring to FIG. 14, in operation 1401, the trustee device 110 sends a request for e-health data to the trustor device 120. In other words, the trustee device 110 sends a request of transmission of health related data to the trustor device 120.

In operation 1403, the trustor device 120 sends a demand for a trust request to the trustee device 110. By the trust request, a security protocol (for example, a handshake protocol) is initialized between the trustor device 120 and the trustee device 110. Through the security protocol, the trustee device 110 receives a request for execution of authentication from the trustor device 120. For example, the trustee device 110 gets a request to perform authentication and send a request for transmission of data including a security ID, from the trustor device 120. In other words, the trustee device 110 receives a request to transmit the security ID from the trustor device 120.

In operation 1405, the trustee device 110 sends a security ID request to the gateway proxy device 140, and the trustor device 120 confirms this ID request. In other words, a process in which the trustee device 110 makes a request for a security ID after receiving the authentication execution request from the trustor device 120 includes a process in which the trustee device 110 sends the security ID request to the gateway proxy device 140.

In operation 1407, the gateway proxy device 140 transmits the security ID to the trustee device 110 in response to the security ID request of the trustee device 110. For example, a process in which the trustee device 110 receives the security ID includes a process in which the trustee device 110 receives the security ID from the gateway proxy device 140.

In operation 1409, the trustee device 110 sends a request for e-health data to the trustor device 120 with the received security ID.

In operation 1411, the trustor device 120 getting the e-health data request together with the security ID performs ID verification through the gateway proxy device 140.

In operation 1413, the gateway proxy device 140 confirms the security ID, and the trustor device 120 identifies the ID request. In other words, the trustor device 120 receives a security ID confirmation response from the gateway proxy device 140.

In operation 1415, the trustor device 120 grants the data access of the trustee device 110 in response together to the e-health data requested by the trustee device 110. For example, the trustor device 120 transmits the requested data to the trustee device 110.

Figure 15:
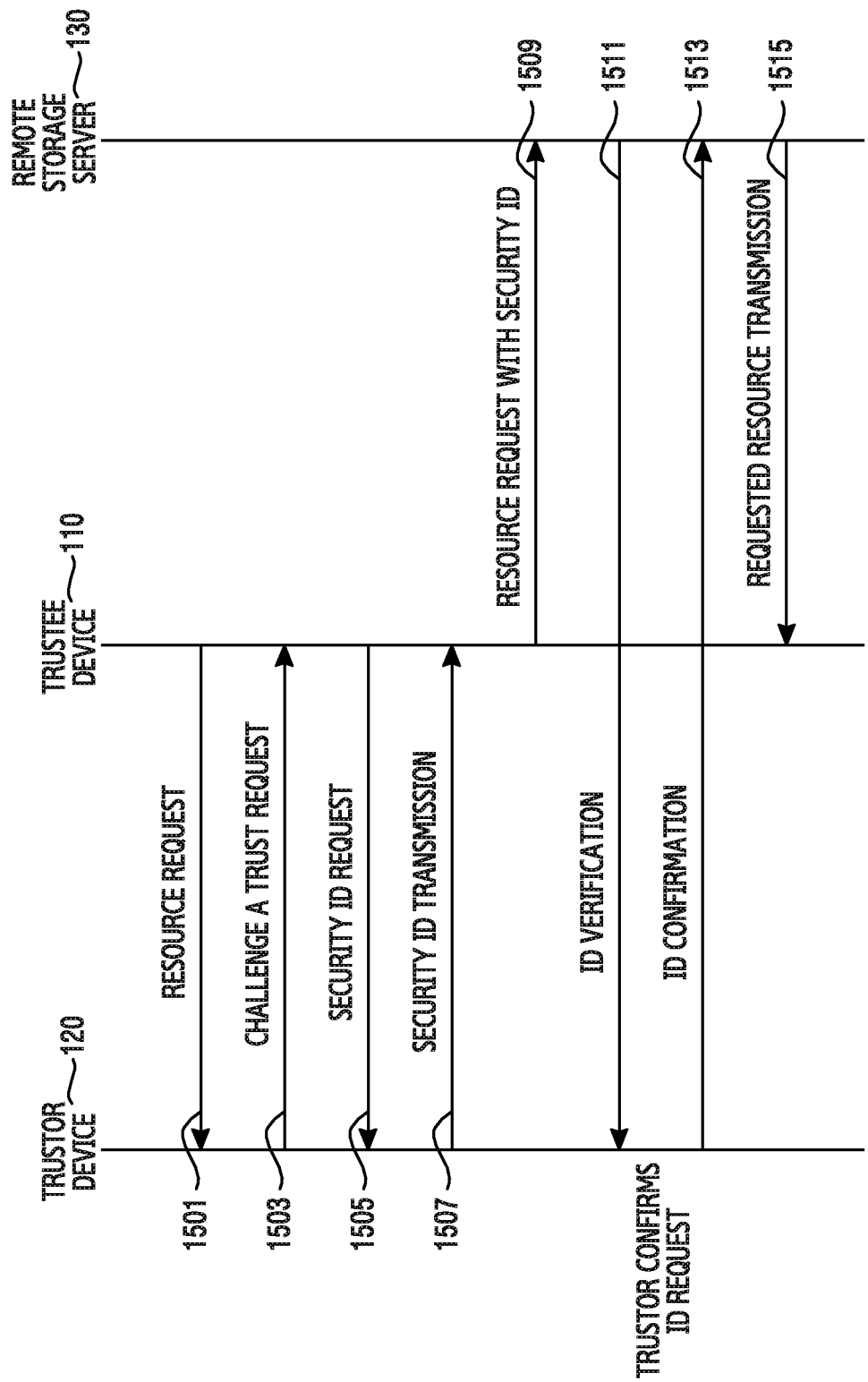
FIG. 15 is a flow diagram of an access control system for secure sharing personal e-health data with remote storage according to an embodiment of the present disclosure.

FIG. 15 is a flow diagram of an access control system for secure sharing personal e-health data with remote storage according to an embodiment of the present disclosure.

Referring to FIG. 15, e-health data that is stored remotely on cloud server can be issued either to the cloud platform, as well as to other server platforms. Storage servers are designed in specific way to contain necessary safety requirements. The process occurs between trustor device 120 and trustee device 110 reflected in FIG. 14. This proxy system is done in trustor's smart device. Once the authentication process to obtain trustor's ID, trustee device 110 will request data to the cloud server. This server will perform a verification proxy system at trustor device 120. If the verification process is successful, the server will send data encrypted e-health data in accordance with security policy embedded in the e-health data.

In operation 1501, the trustee device 110 sends a request for e-health data to the trustor device 120. In other words, the trustor device 120 receives a request for transmission of health related data from the trustee device 110.

In operation 1503, the trustor device 120 sends a demand for a trust request to the trustee device 110. By the trust request, a security protocol (for example, a handshake protocol) is initialized between the trustor device 120 and the trustee device 110. For example, the trustor device 120 sends an authentication execution request to the trustee device 110 in response to the transmission request of the trustee device 110.

In operation 1505, the trustee device 110 sends a security ID request to the trustor device 120. A process of sending the security ID request includes a process in which the trustee device 110 sends the security ID request to the trustor device 120 as a gateway proxy.

In operation 1507, the trustor device 120 transmits a security ID to the trustee device 110. A process of transmitting the security ID includes a process in which the trustor device 120 as the gateway proxy transmits the security ID to the trustee device 110.

Operations 1505 and 1507 can be executed through the gateway proxy device 140.

In operation 1509, the trustee device 110 sends a request for e-health data to the remote storage server 130, with the security ID. In other words, the trustee device 110 transmits a request for transmission of e-health data including the security ID to the remote storage server 130.

In operation 1511, the remote storage server 130 verifies the security ID for the trustor device 120, and the trustor device 120 confirms an ID request. The ID verification of operation 1511 can further include operation in which the trustor device 120 sends a security ID verification request to the gateway proxy server 140, and the trustor device 120 receives a security ID confirmation response from the gateway proxy device 140.

In operation 1513, the trustor device 120 confirms the security ID for the remote storage server 130.

In operation 1515, the remote storage server 130 transmits the requested data to the trustee device 110.

Figure 16:
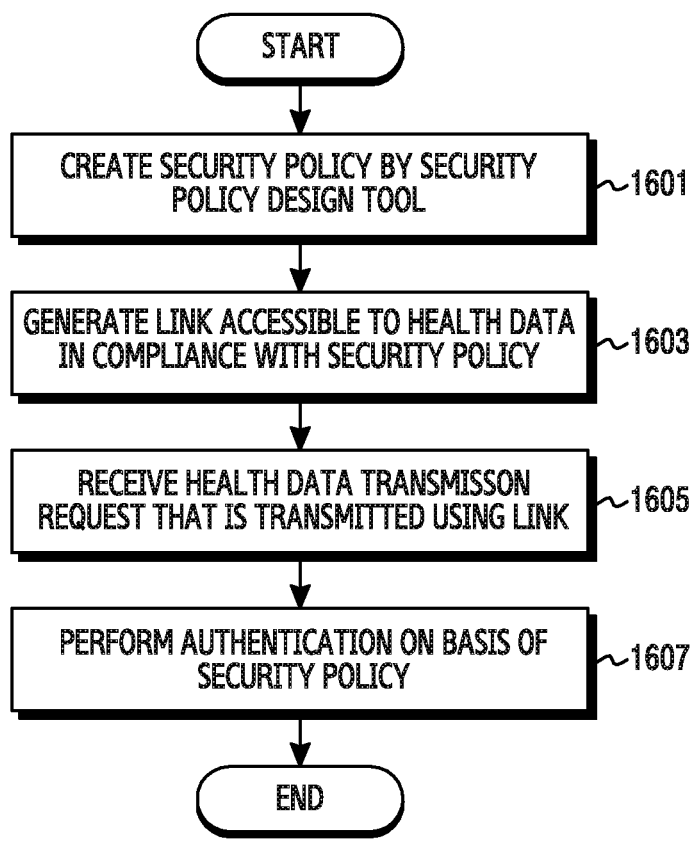
FIG. 16 is a diagram illustrating a procedure for sharing data through a link that is accessible to data applying a security policy according to an embodiment of the present disclosure.

FIG. 16 illustrates a flowchart for sharing data through a link that is accessible to data applying a security policy according to an embodiment of the present disclosure.

Referring to FIG. 16, a flow of a process of sharing data through the link that can gain access to the data to which the security policy for a trustee is applied in a trustor device is given as below.

In operation 1601, the trustor device creates a security policy with a security policy design tool. For example, the trustor device can create the security policy in accordance with at least one user input through the security policy design tool.

In operation 1603, the trustor device creates a link that can gain access to health data in compliance with the security policy. In other words, the trustor device creates the link for gaining access to the health data to be shared in compliance with the security policy. The link can be anyone that is usable as a proper address code such as a URL, a barcode, a QR code or a secret string, and the like. In addition, the link corresponds to at least one of the type of accessible health data, selected in compliance with the security policy, a sharing target of the health data, and/or a sharing period of the health data.

In operation 1605, the trustor device receives a transmitted health data transmission request by using the link. In other words, the trustor device receives the transmitted health data transmission request from a health data request device, using the link. The health data request device can make a request for health data transmission only using a previously created link.

In operation 1607, the trustor device performs authentication on the health data transmission request based on the security policy. In performing the authentication on the health data transmission request that is received through the link, the trustor device performs the authentication based on the security policy corresponding to the link that is accessible to the data to be shared.

Figure 17:
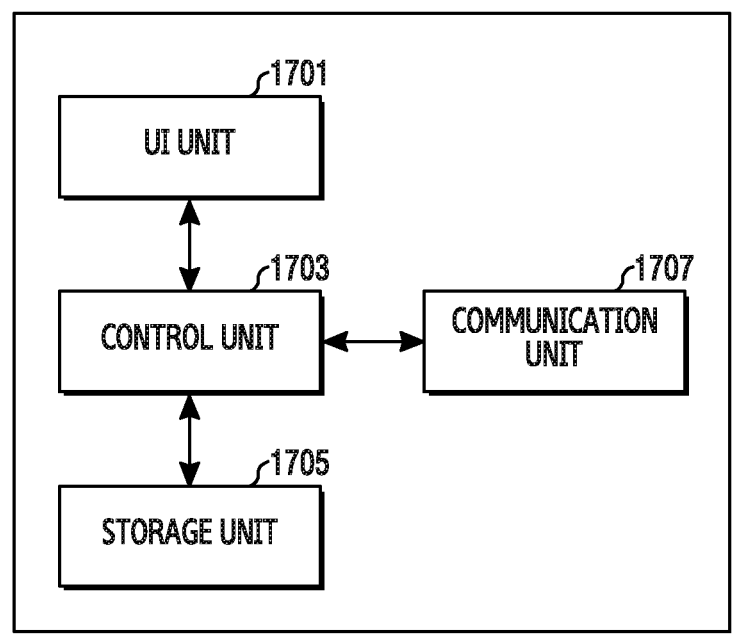
FIG. 17 illustrates a construction of an electronic device according to an embodiment of the present disclosure.

FIG. 17 illustrates a construction of an electronic device according to an embodiment of the present disclosure. The construction of the electronic device illustrated in FIG. 17 can be applied to the trustee device 110 or the trustor device 120.

Referring to FIG. 17, the electronic device includes a UI unit 1701, a control unit 1703, a storage unit 1705 and/or a communication unit 1707.

The UI unit 1701 performs functions of outputting information and detecting a user input. The UI unit 1701 can forward to the control unit 1703 an instruction or data that is inputted from a user. For this, the UI unit 1701 can include at least one hardware module for output and input. For example, the hardware module can include at least one of a sensor, a keyboard, a keypad, a speaker, a microphone, a touch screen, a liquid crystal display (LCD), a light emitting diode (LED), a light emitting polymer display (LPD), an organic LED (OLED), an active matrix OLED (AMOLED), and/or a flexible LED (FLED). For example, the UI unit 1701 can provide the control unit 1703 with data on a user's touch input (e.g., tap, press, pinch, stretch, slide, swipe, rotate, and the like) that is inputted through a touch screen. More particularly, in accordance with an embodiment of the present disclosure, the UI unit 1701 can display information on a current sub operation that is determined by the control unit 1703. In addition, the UI unit 1701 can output an instruction or data received from the control unit 1703, through an input output device (e.g., a speaker or a display). The UI unit 1701 displays a screen and thus, can be denoted as a 'display unit'. In addition, the UI unit 1701 detects a user input and thus, can be denoted as an 'input unit'.

The control unit 1703 controls general operations of the device. For example, the control unit 1703 transceives a signal through the communication unit 1707. In addition, the control unit 1703 records data in the storage unit 1705, and reads. For this, the control unit 1703 can include at least one processor or micro-processor, or be a part of the processor. In addition, a part of the communication unit 1707 and the control unit 1703 can be denoted as a communication processor (CP). In accordance with an embodiment of the present disclosure, the control unit 1703 installs and executes a security client application in the trustee device 110, and controls the reception of a security ID and e-health data through the security client application. In addition, in case where the security client application is not used or a preset specific period of time elapses, the control unit 1703 deletes the security client application from the storage unit 1705. In accordance with another embodiment of the present disclosure, the control unit 1703 executes a trust management application in the trustor device 120. In addition, the control unit 1703 determines a security policy in accordance with a user input for selection and combination of at least one of security attribute items. Further, for the sake of a data requestor, the control unit 1703 creates a link that is accessible to related data in compliance with the security policy. In addition, the control unit 1703 can perform encryption by combining data corresponding to the security policy and biometric information of at least one of fingerprint, iris and/or face.

The control unit 1703 can control the device to perform the procedures illustrated in FIGS. 7 to 9, 10A and 10B, and 11 to 16.

The storage unit 1705 stores data such as a basic program for an operation of the device, an application program, setting information, and the like. More particularly, the storage unit 1705 can store a security client application for e-health data sharing or a trust management application. In addition, the storage unit 1705 can store e-health data such as a blood pressure, a heart rate, a blood type, a blood sugar level, and the like, that are measured by the trustor. And, the storage unit 1705 provides the stored data in accordance with a request of the control unit 1703.

The communication unit 1707 performs functions for transceiving a signal through a wireless channel For example, the communication unit 1707 performs a function of conversion between a baseband signal and a bit stream in compliance with the physical layer standard of a system. For example, at data transmission, the communication unit 1707 creates complex symbols by encoding and modulating a transmission bit stream. In addition, at data reception, the communication unit 1707 restores a reception bit stream by demodulating and decoding a baseband signal. In addition, the communication unit 1707 up converts a baseband signal into a radio frequency (RF) band signal and then transmits the RF band signal through an antenna, and down converts an RF band signal received through the antenna into a baseband signal. For example, the communication unit 1707 may include a transmission filter, a reception filter, an amplifier, a mixer, an oscillator, a digital to analog converter (DAC), an analog to digital converter (ADC), and the like.

In addition, the communication unit 1707 can include a plurality of RF chains. Further, the communication unit 1707 can perform beamforming For the sake of beamforming, the communication unit 1707 can adjust a phase and magnitude of each of signals that are transceived through a plurality of antennas or antenna elements. Further, the communication unit 1707 can include a plurality of communication modules so as to support a plurality of different wireless access technologies.

In addition, the communication unit 1707 can include different communication modules so as to process different frequency-band signals. For example, different communication standards can include Bluetooth low energy (BLE), Wi-Fi, Wi-Fi Gigabyte (WiGig), a cellular network (e.g., long term evolution (LTE), and the like. In addition, different frequency bands can include a super high frequency (SHF) (e.g., 2.5 GHz, 5 GHz) band, and/or a millimeter (mm) wave (e.g., 60 GHz) band.

The communication unit 1707 transmits and receives a signal as mentioned above. In accordance with this, the communication unit 1707 can be denoted as a transmission unit, a reception unit or a transceiving unit. In addition, in the following description, transmission and reception performed through a wireless channel are used as a meaning including that the aforementioned processing is performed by the communication unit 1707.

In case where the electronic device of FIG. 17 is the trustee device 110, the trustee device 110 is comprised of the storage unit 1705 storing information necessary for an operation of the electronic device, the communication unit 1707 performing communication with a health data share device, and the control unit 1703 controlling the storage unit 1705 and the communication unit 1707. The communication unit 1707 sends a health data transmission request to the trustor device 120 by using a link complying to a security policy, and receives from the trustor device 120 a security ID transmission request responsive to the transmission request, and after the security ID transmission request reception, for example, sends a security ID request to the gateway proxy device 140, and receives a security ID from the gateway proxy device 140, and sends a health data transmission request to the trustor device 120 using the security ID, and receives health data.

In case where the electronic device of FIG. 17 is the trustor device 120, the trustor device 120 is comprised of the storage unit 1705 storing one or more applications including a trust management application, the control unit 1703 executing the trust management application, the communication unit 1707 performing communication with a health data request device, and the display unit 1701 displaying a UI of the trust management application. The display unit 1701 displays one or more icons including a security policy design tool creating a security policy template and, if a security policy design tool icon is selected, the display unit 1701 displays items representing logic attributes and security attributes. The control unit 1703 determines a security policy in accordance with a user input for selection and combination of at least one of the items, and creates a data access link complying with the security policy. The communication unit 1707 receives a request for data transmission making use of an access link, from the trustee device 110.

Methods according to various embodiments mentioned in claims or specification of the present disclosure can be implemented in a form of hardware, software, or a combination of hardware and software.

Certain aspects of the present disclosure can also be embodied as computer readable code on a non-transitory computer readable recording medium. A non-transitory computer readable recording medium is any data storage device that can store data which can be thereafter read by a computer system. Examples of the non-transitory computer readable recording medium include a Read-Only Memory (ROM), a Random-Access Memory (RAM), Compact Disc-ROMs (CD-ROMs), magnetic tapes, floppy disks, and optical data storage devices. The non-transitory computer readable recording medium can also be distributed over network coupled computer systems so that the computer readable code is stored and executed in a distributed fashion. In addition, functional programs, code, and code segments for accomplishing the present disclosure can be easily construed by programmers skilled in the art to which the present disclosure pertains.

At this point it should be noted that the various embodiments of the present disclosure as described above typically involve the processing of input data and the generation of output data to some extent. This input data processing and output data generation may be implemented in hardware or software in combination with hardware. For example, specific electronic components may be employed in a mobile device or similar or related circuitry for implementing the functions associated with the various embodiments of the present disclosure as described above. Alternatively, one or more processors operating in accordance with stored instructions may implement the functions associated with the various embodiments of the present disclosure as described above. If such is the case, it is within the scope of the present disclosure that such instructions may be stored on one or more non-transitory processor readable mediums. Examples of the processor readable mediums include a ROM, a RAM, CD-ROMs, magnetic tapes, floppy disks, and optical data storage devices. The processor readable mediums can also be distributed over network coupled computer systems so that the instructions are stored and executed in a distributed fashion. In addition, functional computer programs, instructions, and instruction segments for accomplishing the present disclosure can be easily construed by programmers skilled in the art to which the present disclosure pertains.

Further, the program can be stored in an attachable storage device that can access through a communication network such as the Internet, an intranet, a local area network (LAN), a wireless LAN (WLAN) and a storage area network (SAN), or a communication network constructed in combination of them. This storage device can connect to a device performing an embodiment of the present disclosure through an external port. In addition, a separate storage device on the communication network may connect to the device performing the embodiment of the present disclosure.

In the aforementioned concrete various embodiments of the present disclosure, constituent elements included in the disclosure have been expressed in the singular form or plural form in accordance to a proposed concrete embodiment. But, the expression of the singular form or plural form is selected suitable to a proposed situation for description convenience, and it is not that the present disclosure is limited to singular or plural constituent elements. Even a constituent element expressed in the plural form can be constructed in the singular form, or even a constituent element expressed in the singular form can be constructed in the plural form.

This disclosure discloses the system and method for trust management in personal e-health to manage trust between patient and second party in sharing medical records in dynamic and un-trusted environment.

Technology disclosed in this disclosure can be applied to any kind of smart devices to protect personal health data. Communication between user's devices and second parties will be arranged by a secure protocol that can preserve users' privacy in sharing medical records. The flexibility is also considered by enabling the data to be stored either in local smart device or secure remote server. Through this method, the system can provide a secure and reliable data transaction for both the patients and second parties such as doctors, friends, family, and the like.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An operation method of an electronic device for sharing health data, the method comprising:
   identifying, by at least one processor of the electronic device, biometric information for a user of the electronic device and security information including an identifier about a group of users accessible to the health data and expire date time for the health data based on at least one input of the user of the electronic device;
   storing the security information and the biometric information for the user of the electronic device;
   receiving, from a health data request device via a gateway proxy device, a first transmission request for health data;
   transmitting, to the health data request device via the gateway proxy device, a request for security ID;
   confirming a request for the security ID, the request for the security ID being transmitted from the health data request device to the gateway proxy device;

obtaining, by a transceiver of the electronic device, a second transmission request for the health data from a health data request device, wherein the second transmission request comprises an identifier of the health data request device and the security ID;

based on the gateway proxy device validating the security ID and identifying that the identifier of the health data request device matches the stored identifier and a reception time of the transmission request is before the expire date time, displaying a user interface for requesting biometric information of the user;

identifying health data to be transmitted based on a security policy associated with the health data; and transmitting, in accordance with the security policy associated with the identified health data, the identified health data to the health data request device after authenticating the user using the stored biometric information and biometric information received through the user interface, wherein the security ID is generated by the gateway proxy device and transmitted to the health data request device after the confirmation of the request for the security ID.

2. The method of claim 1, further comprising:

encrypting the health data, to be shared by a link for gaining access to the health data, by using the stored biometric information of at least one of a fingerprint, an iris or a face based on the security information, the link specifying the health data to be transmitted.

3. The method of claim 2, wherein the link corresponds to at least one of a type of accessible health data that is selected according to the security information, a sharing target of the health data, or a sharing period of the health data.

4. The method of claim 2, wherein the link comprises one of a barcode, a uniform resource locator (URL) address, or a quick response (QR) code.

5. The method of claim 1, further comprising:

controlling to transmit the health data to the health data request device through a remote storage device, after performing the authentication on the transmission request.

6. The method of claim 1, further comprising:

displaying one or more icons comprising an icon associated with security for the health data;

displaying, when the icon associated with security for the health data is selected, items indicating logic attributes and security attributes; and identifying the security information in accordance with the at least one input of the user of the electronic device for selection and combination of at least one of the items.

7. The method of claim 6, further comprising:

displaying the items and a region for the selection and combination of the at least one items; and identifying the security information based on at least one item that is dragged to the region or clicked by the user of the electronic device.

8. An electronic device for sharing health data, the electronic device comprising:

a display;

a transceiver; and at least one processor configured to:

identify biometric information for a user of the electronic device and security information including an identifier about a group of users accessible to the health data and expire date time for the health data based on at least one input of the user of the electronic device, store the security information and the biometric information for the user of the electronic device, receive, from a health data request device via a gateway proxy device, a first transmission request for health data, transmit, to the health data request device via the gateway proxy device, a request for security ID, confirm a request for the security ID, the request for the security ID being transmitted from the health data request device to the gateway proxy device, obtain, by the transceiver, a second transmission request for the health data from a health data request device, wherein the second transmission request comprises an identifier of the health data request device and the security ID, based on the gateway proxy device validating the security ID and identifying that the identifier of the health data request device matches the stored identifier and a reception time of the transmission request is before the expire date time, control the display to display a user interface for requesting biometric information of the user, identify health data to be transmitted based on a security policy associated with the health data, wherein the transceiver is configured to transmit, in accordance with the security policy associated with the identified health data, the identified health data to the health data request device after authenticating the user using the stored biometric information and biometric information received through the user interface, and wherein the security ID is generated by the gateway proxy device and transmitted to the health data request device after the confirmation of the request for the security ID.

9. The electronic device of claim 8, wherein the at least one processor is further configured to encrypt the health data to be shared by a link for gaining access to the health data by using the stored biometric information of at least one of a fingerprint, an iris or a face based on the security information, the link specifying the health data to be transmitted.

10. The electronic device of claim 9, wherein the link corresponds to at least one of a type of accessible health data that is selected according to the security information, a sharing target of the health data or a sharing period of the health data.

11. The electronic device of claim 9, wherein the link comprises one of a barcode, a uniform resource locator (URL) address or a quick response (QR) code.

12. The electronic device of claim 8, wherein the at least one processor is further configured to control to transmit the health data to the health data request device through a remote storage device, after performing an authentication on the transmission request.

13. The electronic device of claim 8, further comprising:

a display configured to display a user interface (UI), wherein the display is further configured to:

display one or more icons comprising an icon associated with security for the health data, and display items indicating logic attributes and security attributes when the icon associated with security for the health data is selected, and wherein the at least one processor is further configured to identify the security information in accordance with the at least one input of the user of the electronic device for selection and combination of at least one of the items.

14. The electronic device of claim 13,
wherein the display is further configured to display the items and a region for the selection and combination of the at least one items, and
wherein the at least one processor is further configured to identify the security information based on at least one item that is dragged to the region or clicked by the user of the electronic device.

\* \* \* \* \*